(12) United States Patent
Ito et al.

(10) Patent No.: US 6,920,200 B2
(45) Date of Patent: Jul. 19, 2005

(54) DENSITY-NONUNIFORM MULTILAYER FILM ANALYZING METHOD, AND APPARATUS AND SYSTEM THEREOF

(75) Inventors: Yoshiyasu Ito, Tokyo (JP); Kazuhiko Omote, Tokyo (JP)

(73) Assignee: Rigaku Corporation, Tokyo (JP)

( * ) Notice: Subject to any disclaimer, the term of this patent is extended or adjusted under 35 U.S.C. 154(b) by 168 days.

(21) Appl. No.: 10/455,611

(22) Filed: Jun. 6, 2003

(65) Prior Publication Data

US 2004/0066893 A1 Apr. 8, 2004

(30) Foreign Application Priority Data

Jun. 6, 2002 (JP) ........................................ 2002-165365

(51) Int. Cl.[7] .............................................. G01B 15/02
(52) U.S. Cl. ........................................................ 378/89
(58) Field of Search ............................................ 378/89

(56) References Cited

U.S. PATENT DOCUMENTS 4,641,030 A * 2/1987 Regimand .................... 250/308
6,421,415 B1 * 7/2002 Peczkis et al. ................. 378/46

* cited by examiner

Primary Examiner—Craig E. Church
Assistant Examiner—Thomas R Artman
(74) Attorney, Agent, or Firm—Wenderoth, Lind & Ponack, L.L.P.

(57) ABSTRACT

Provided is a novel density-nonuniform multilayer analyzing method that readily and highly accurately enables analyzing the state of distribution and interfacial condition of particulate matter in a density-nonuniform multilayer film. The method includes the step of, by using a scattering function representing an X-ray scattering curve according to a fitting parameter indicating a state of distribution of particulate matter, calculating a simulated X-ray scattering curve under the same conditions as those under which an actually measured X-ray scattering curve is measured, and the step of performing fitting between the simulated X-ray scattering curve and the actually measured X-ray scattering curve while the fitting parameter is being changed. The values of the fitting parameters that have been used when the simulated X-ray scattering curve and the actually measured X-ray scattering curve have coincided with each other are regarded as representing the state of distribution of the particulate matter in the density-nonuniform multilayer film. By doing so, there is analyzed the state of distribution of the particulate matter within the density-nonuniform multilayer film. In this case, as the scattering function, there is used a function into which there has been introduced the transition probability wherein the exact solutions of the multilayer film where no scattering occurs at the interfaces are set to be an initial state and a final state.

12 Claims, 19 Drawing Sheets

(a)

(b)

(a) $\left|\langle-\zeta_i^-|V_i|n_i\rangle\right|^2$ (b) $\left|\bar{\varphi}_i^2\langle\zeta_i^-|V_i|n_i\rangle\right|^2$ (c) $\left|\varphi_i^2\langle-\zeta_i^-|V_i|-n_i\rangle\right|^2$ (d) $\left|\bar{\varphi}_i^2\varphi_i^2\langle\zeta_i^-|V_i|-n_i\rangle\right|^2$

DENSITY-NONUNIFORM MULTILAYER FILM ANALYZING METHOD, AND APPARATUS AND SYSTEM THEREOF

BACKGROUND OF THE INVENTION

1. Field of the Invention

The invention of the present application relates to a density-nonuniform multilayer film analyzing method, and an apparatus and system thereof. More particularly, the invention of the present application relates to a novel density-nonuniform multilayer film analyzing method, density-nonuniform multilayer film analyzing apparatus, and density-nonuniform multilayer film analyzing system each of which enables readily and highly accurately analyzing the state of distribution and the interfacial condition of particulate matter in a density-nonuniform multilayer film.

2. Description of the Related Art

As a technique for analyzing and evaluating the non-uniformity of the density of a density-nonuniform specimen such as a porous film where particulate matter such as fine particles and pores lies scattered, a new method for analyzing the pore size distribution in the density-nonuniform specimen by using an X-ray has already been proposed, by the inventors of the invention of this application (see Japanese Patent Application No. 2001-088656). That analyzing method is the one which measures the diffuse scattering strength of an X-ray and, according to the measured values, analyzes the hole diameter distribution, and realizes an excellent level of analyzing performance.

However, although the analyzing method is an excellent one like that, through further studies and development made by the inventors of the invention of this application, that technique has turned out to have the respects with respect to which further improvement should be made.

In more detail, since, in the density-nonuniform analyzing method described in Japanese Patent Application No. 2001-088656, density-nonuniform analysis is performed which is based on considering the diffuse scattering phenomena within a single-layer film, applying it to a multilayer film specimen leads to the possibility that there will occurs a case where analyzing accuracy becomes lowered because of no consideration being given to the effects of the diffuse scattering in each layer. In addition, regarding the reflection effect at the surface or interface, it is taken into consideration only once and multiple reflections are not considered. Therefore, there is the room for further enhancing the accuracy, too.

SUMMARY OF THE INVENTION

The invention of the present application has been made in view of the above-described circumstances and has an object to provide a novel density-nonuniform multilayer film analyzing method, density-nonuniform multilayer film analyzing apparatus, and density-nonuniform multilayer film analyzing system each of which enables readily and highly accurately analyzing the state of distribution of particulate matter in a density-nonuniform multilayer film.

As the techniques for attaining the above object, a first aspect of the invention of the present application provides a density-nonuniform multilayer analyzing method comprising the step of, by using a scattering function representing an X-ray scattering curve according to a fitting parameter indicating a state of distribution of particulate matter, the step of calculating a simulated X-ray scattering curve under the same conditions as those under which an actually measured X-ray scattering curve is measured, and the step of performing fitting between the simulated X-ray scattering curve and the actually measured X-ray scattering curve while the fitting parameter is being changed, the values of the fitting parameters that have been used when the simulated X-ray scattering curve and the actually measured X-ray scattering curve have coincided with each other being regarded as representing the state of distribution of the particulate matter in the density-nonuniform multilayer film, to thereby analyze the state of distribution of the particulate matter within the density-nonuniform multilayer film, wherein as the scattering function, there is used a function into which there has been introduced the transition probability wherein the exact solutions of the multilayer film are set to be an initial state and a final state.

A second aspect of the invention provides a density-nonuniform multilayer analyzing method comprising the step of, by using a scattering function representing a corpuscular-ray scattering curve according to a fitting parameter indicating a state of distribution of particulate matter, the step of calculating a simulated corpuscular-ray scattering curve under the same conditions as those under which an actually measured corpuscular-ray scattering curve is measured, and the step of performing fitting between the simulated corpuscular-ray scattering curve and the actually measured corpuscular-ray scattering curve while the fitting parameter is being changed, the values of the fitting parameters that have been used when the simulated corpuscular-ray scattering curve and the actually measured corpuscular-ray scattering curve have coincided with each other being regarded as representing the state of distribution of the particulate matter in the density-nonuniform multilayer film, to thereby analyze the state of distribution of the particulate matter within the density-nonuniform multilayer film, wherein as the scattering function, there is used a function into which there has been introduced the transition probability wherein the exact solutions of the multilayer film are set to be an initial state and a final state.

A third aspect of the invention provides a density-nonuniform multilayer analyzing method wherein, as the scattering function, there is used the transition-probability introduced function into which there has further been introduced a fitting parameter representing an interfacial condition.

A fourth aspect of the invention provides a density-nonuniform multilayer analyzing apparatus comprising function storage means for storing therein a scattering function representing an X-ray scattering curve according to a fitting parameter indicating a state of distribution of particulate matter, simulating means for, by using a scattering function representing sent from the function storage means, calculating a simulated X-ray scattering curve under the same conditions as those under which an actually measured X-ray scattering curve is measured, and fitting means for performing fitting between the simulated X-ray scattering curve and the actually measured X-ray scattering curve while the fitting parameter is being changed, the values of the fitting parameters that have been used when the simulated X-ray scattering curve and the actually measured X-ray scattering curve have coincided with each other being regarded as representing the state of distribution of the particulate matter in the density-nonuniform multilayer film, to thereby analyze the state of distribution of the particulate matter within the density-nonuniform multilayer film, wherein the scattering function is a function into which there has been introduced the transition probability wherein the exact solutions of the multilayer film are set to be an initial state and a final state.

A fifth aspect of the invention provides a density-nonuniform multilayer analyzing apparatus comprising function storage means for storing therein a scattering function representing a corpuscular-ray scattering curve according to a fitting parameter indicating a state of distribution of particulate matter, simulating means for, by using a scattering function representing sent from the function storage means, calculating a simulated corpuscular-ray scattering curve under the same conditions as those under which an actually measured corpuscular-ray scattering curve is measured, and fitting means for performing fitting between the simulated corpuscular-ray scattering curve and the actually measured corpuscular-ray scattering curve while the fitting parameter is being changed, the values of the fitting parameters that have been used when the simulated corpuscular-ray scattering curve and the actually measured corpuscular-ray scattering curve have coincided with each other being regarded as representing the state of distribution of the particulate matter in the density-nonuniform multilayer film, to thereby analyze the state of distribution of the particulate matter within the density-nonuniform multilayer film, wherein the scattering function is a function into which there has been introduced the transition probability wherein the exact solutions of the multilayer film are set to be an initial state and a final state.

A sixth aspect of the invention provides a density-nonuniform multilayer analyzing apparatus, wherein the scattering function is the transition-probability introduced function into which there has further been introduced a fitting parameter representing an interfacial condition.

Also, further, another aspect of the invention of the present application provides a density-nonuniform multilayer analyzing system being adapted to analyze a state of distribution of particular matter within a density-nonuniform multilayer film, comprising an X-ray measuring device for measuring an actually measured X-ray scattering curve of the density-nonuniform multilayer film or corpuscular-ray measuring device for measuring an actually measured corpuscular-ray scattering curve of the density-nonuniform multilayer film and the above-described density-nonuniform multilayer analyzing apparatus.

DESCRIPTION OF THE PREFERRED EMBODIMENTS

In the invention of this patent application, on a substrate one or more density-nonuniform films are laminated. Namely, the present invention aims to realize high-accuracy analysis of the non-uniformity of density that is made with respect to a density-nonuniform multilayer film composed of two or more layers including the substrate. To this end, the invention uses, as the scattering function which represents an X-ray scattering curve according to fitting parameters that represent the state of distribution of particulate matter, in the analysis method described in Japanese patent application No. 2001-088656, a function into which there is introduced the transition probability where the exact solutions of the multilayer film are set as initial state and final state.

The idea on the transition probability is already established in the theory of distorted wave born approximation (=DWBA: Distorted Wave Born Approximation). The invention of this patent application has the greatest characteristic in that it uses, as the initial and final states of the transition probability of that DWBA theory, the exact solutions of a density-nonuniform, non-scattered, ideal multilayer film. In this exact solution, consideration is taken of multiple reflection phenomena in the multilayer film.

Figure 1:
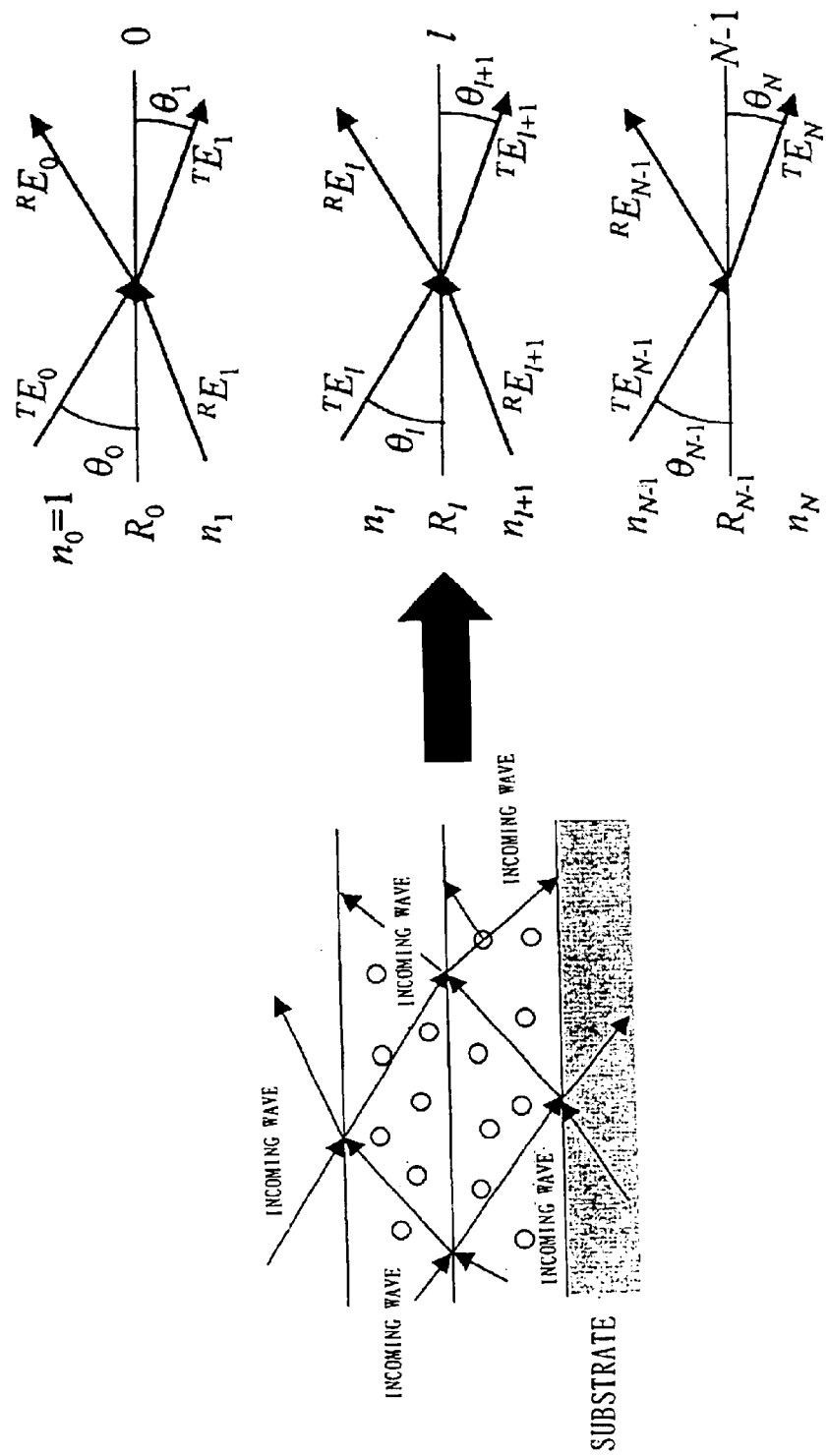
FIG. 1 is a schematic view illustrating what the electric field within a density-nonuniform multilayer film having a multilayer structure the number of whose layers is N is alike.

More specifically, first, as exemplified in, for example, in FIG. 1, when X-rays or corpuscular rays have been radiated with respect to a multilayer film having an N number of layers, a wave $^T E_O$ that has been incident upon the surface of a specimen at an incident angle $\theta_O$ is refracted at the surface of specimen at an angle of $\theta_1$ to go toward a next layer. Subsequently, this wave $^T E_1$ is incident upon an interface between the surface layer and the next layer at an angle of $\theta_1$ and is refracted there at an angle of $\theta_2$. Thereafter, the same phenomenon goes on at each layer and each interface. Namely, the incident wave continues to go on through each layer while repeatedly refracted at each interface ($^T E_O \to ^T E_l \to \ldots ^T E_l \to ^T E_{l+1} \to \ldots \to ^T E_{N-1} \to ^T E_{N-1} \to ^T E_N$). Also, since the incident wave is not only refracted at each interface but are there also cases where it is reflected to go back to the upper layer, there also occur phenomena where the wave that has been reflected by the interface between the upper layer and the immediately lower layer further goes on to the again upper layer ($^R E_{N-1} \to \ldots \to ^R E_{l+1} \to ^R E_l \to \ldots \to ^R E_l \to ^R E_O$). And these phenomena and reflection occurring from the incident wave can respectively be expressed by the following expressions. It is to be noted here that the term "interface" is used as the one having not only the interface between the film layers but also the "interface between the outside (e.g. aerial layer) and the surface layer" and, when referring only to the surface of the surface layer in particular, the "interface" is referred to as the "specimen surface".

Refraction phenomenon = $^T E_1(z_1) = \prod_{j=1}^{l-1} (t_j, \varphi_j) e^{ik_0 \alpha_1 z_1}$ [Expression 1]

Reflection phenomenon =

$^R E_1(z_1) = \prod_{j=1}^{l-1} (t_j, \varphi_j)(R_1 \varphi_1) e^{ik_0 \alpha_1 z_1}$ where $E_l$ = Strength of wave field in each layer $k_0 = \frac{2\pi}{\lambda}$ = Wave vector of incidend wave on the surface (known value)

$\lambda$ = Wavelength of the incident wave = wavelength of the outgoing wave (known value)

$\alpha_l = \sqrt{n_l - \cos^2 \theta_0}$ = Refracted angle at each interface (known value)

$n_l$ = Refractive index of each layer (known value)

$\theta_0$ = Incident angle to the surface (known value)

$\varphi_l = e^{ik_0 \alpha_l d_l}$ = Phase factor when the wave propagates through each layer (known value)

$d_l = Z_l$ = Depth from each interface (known value)

$t_1 = \frac{1 - \gamma_1 R_1}{\tau_1} = $ Transmitted coefficient at each interface each layer (known value)

$R_1 = \frac{R_{l+1} \varphi_{l+1}^2 + \gamma_1}{R_{l+1} \varphi_{l+1}^2 \gamma_1 + 1} = $ Reflection coefficient at each interface (known value)

$\gamma_1 = \frac{\alpha_1 - \alpha_{l+1}}{\alpha_1 + \alpha_{l+1}} = $ Frenell's coefficient at each interface (known value)

$\tau_1 = \frac{2\alpha_{l+1}}{\alpha_1 + \alpha_{l+1}}$ l = Layer numbers 0 . . . N In this refraction phenomenon expression, each time that the wave advances in the way of the upper layer→the lower layer, the $t_1$ and the $\varphi_1$ are each applied to each layer while, on the other hand, in the reflection phenomenon expression, each time that after reflection the wave advances in the way of from the lower layer→the upper layer, the $t_l$ and the $\varphi_l$ are each applied to each layer and, at the same time, the $R_l$ and the $\varphi_l$ are each applied thereto.

Figure 2:
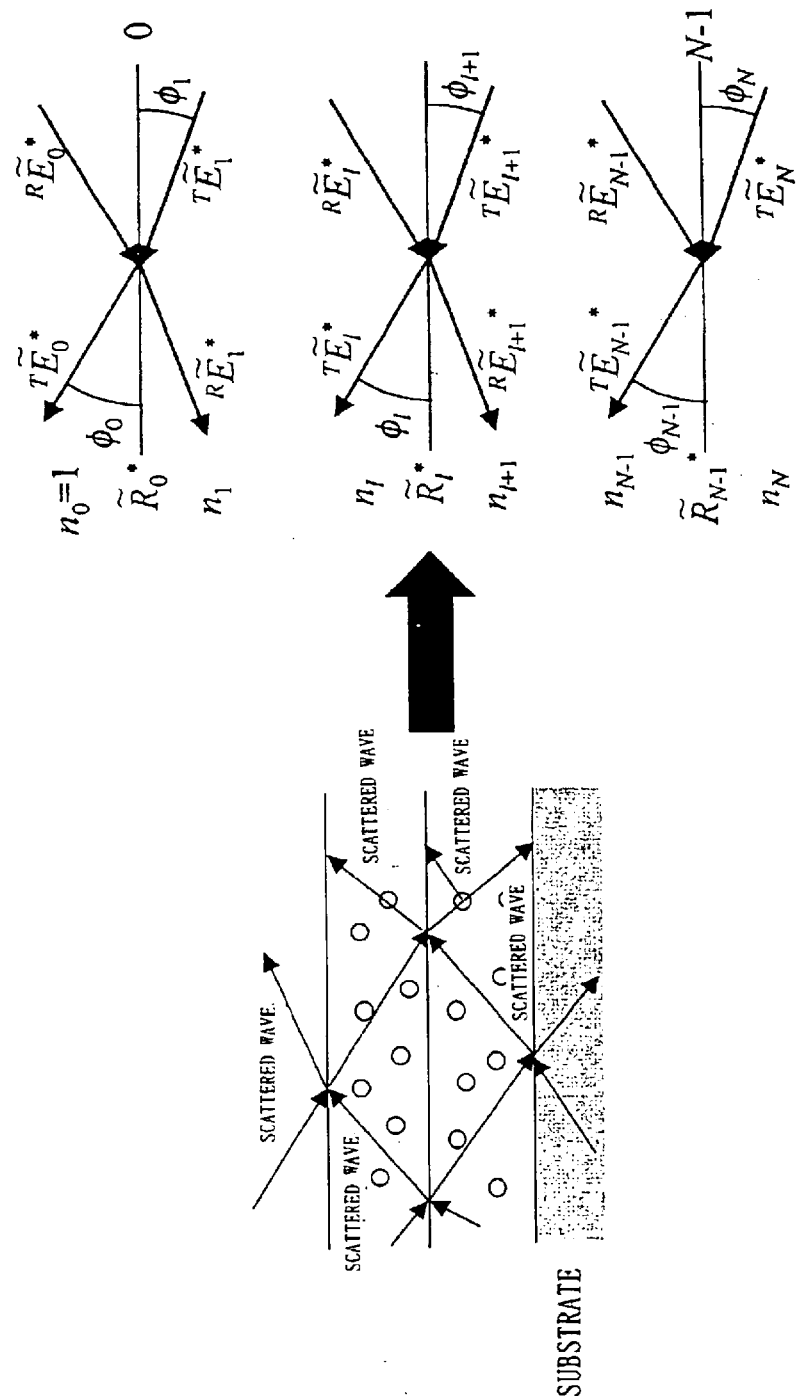
FIG. 2 is a schematic view illustrating what the electric field within a density-nonuniform multilayer film having a multilayer structure the number of whose layers is N is alike.

On the other hand, as exemplified in, for example, FIG. 2, in the case where the incident wave is scattered by the particulate matter during a time period in which it advances through the layer, toward the upper layer and goes out from the specimen surface, the wave propagates completely conversely to that in the case of FIG. 1. Namely, while it is being repeatedly refracted and reflected at each layer and each interface, the wave goes on through in the way of $^T E_N^* \to ^T E_{N-1}^* \to \ldots \to ^T E_{l+1}^* \to ^T E_l^* \to \ldots \to ^T E1_l^* \to ^T E_O^*$ and returns in the way of $^R E_O \to ^R E_l \to \ldots \to ^R E_l \to ^R E_{l+1} \to \ldots \to ^R E_{N-1}$. Namely, the phenomenon of the scattered X-ray is the reversal from the phenomenon of the incoming X-ray and, if this is looked at from the substrate side, is considered to be the same phenomenon as that which occurs when the X-ray comes in. Incidentally, although not added, the "E's" described above are each the one added with the mark tilde "" that means the time reversal, and the superscript "*" represents the complex conjugate. The wave phenomenon with the superscript "*" indicates the one that has been obtained by determining the complex conjugate and performing the time reversal and by the phenomenon's of the incoming X-ray being reversed. The refraction phenomenon and reflection phenomenon with respect to that outgoing wave can respectively be expressed by the following expressions.

Refraction phenomenon = [Expression 2]

$^T \tilde{E}_1^*(z_1) = \prod_{j=1}^{l-1} (t_j \varphi_j)^* e^{-ik_0 \zeta_1^* z_1}$ Reflection phenomenon =

$^R \tilde{E}_1^*(z_1) = \prod_{j=1}^{l-1} (\tilde{t}_j \tilde{\varphi}_j)^* (\tilde{R}_1 \tilde{\varphi}_1)^* e^{-ik_0 \zeta_1^* z_1}$ where $E_l$ = Strength of wave field in each layer $k_0 = \frac{2\pi}{\lambda}$ = Wave vector of scattered wave on the surface (known value)

$\lambda$ = Wavelength of the scattered wave = wavelength of the incoming wave (known value)

$\zeta_l = \sqrt{n_l - \cos^2 \phi_0}$ $n_l$=Refractive index of each layer (known value)

$\phi_0$=Exit angle to the surface (known value)

$\phi_l^* = e^{ik_0\zeta_l^* d_l}$=Phase factor when the wave propagates through each layer (known value)

$d_l = Z_l$=Depth from each interface (known value)

$\tilde{t}_1^* = \dfrac{1 - \tilde{\gamma}_1^* \tilde{R}_1^*}{\tilde{t}_{1*}}$ = Transmitted coefficient at each interface (known value)

$\tilde{R}_1^* = \dfrac{\tilde{R}_{l+1}\tilde{\varphi}_{l+1}^{*2} + \tilde{\gamma}_1^*}{\tilde{R}_{l+1}^*\tilde{\varphi}_{l+1}^{*2}\tilde{\gamma}_1^* + 1}$ = Reflection coefficient at each interface (known value)

$\tilde{\gamma}_1^* = \dfrac{\zeta_1^* - \zeta_{l+1}^*}{\zeta_1^* + \zeta_{l+1}^*}$ = Reflection coefficient (Frenell's coefficient) (known value)

$\tilde{t}_1^* = \dfrac{2\zeta_{l+1}}{\zeta_1^* + \zeta_{l+1}^*}$ l=Layer numbers 0 ... N In this refraction phenomenon expression, each time that the wave advances in the way of the upper layer→the lower layer, the $t_l$ and the $\phi_l$ are each applied to each layer while, on the other hand, in the reflection phenomenon expression, each time that after reflection the wave advances in the way of from the lower layer→the upper layer, the $t_l$ and the $\phi_l$ are each applied to each layer and, at the same time, the $R_l$ and the $\phi_l$ are each applied thereto.

Figure 3:
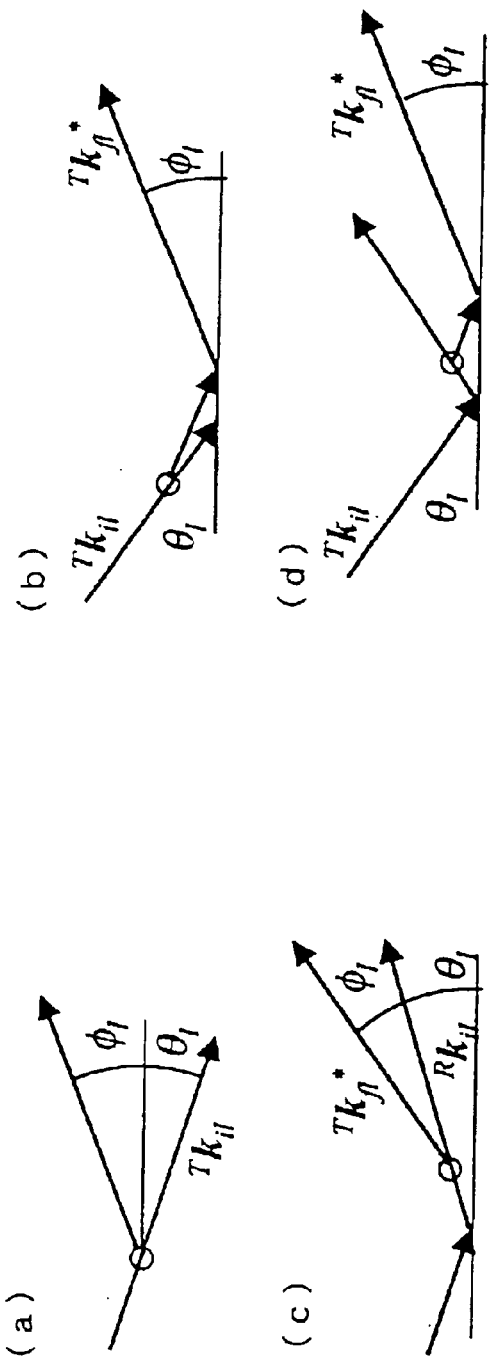
FIGS. 3A to 3D are schematic views illustrating various kinds of multiple phenomena.

In the invention of this patent application, as described above, the transition probability regarding the incident and outgoing waves that is based on the consideration of the diffuse scattering phenomena in the multilayer film has been introduced into the scattering function. By doing so, the density non-uniformity of the multilayer film can be analyzed with a high accuracy. However, further, by simultaneously considering various phenomena, as well, including the multiple reflections that have been exemplified in FIGS. 3A to 3D, further enhancement of the accuracy is realized. FIG. 3A represents the phenomenon wherein the incident wave is scattered by the particulate matter in the 1st layer; FIG. 3B represents the phenomenon wherein the incident wave scattered by the particulate matter is further reflected by the interface; FIG. 3C represents the phenomenon wherein the incident wave reflected by the interface is further scattered by the particulate matter; and FIG. 3D represents the phenomenon wherein the incident wave reflected by the interface is further scattered by the particulate matter and then the resulting wave is further reflected by the interface to present multiple reflection phenomena. Taking into consideration the above-described multilayer diffuse scattering phenomena including those multiple reflection phenomena, the transition probability based on the consideration thereof is established. The following expression is an example of the transition probability in that case.

Amplitude of Transition probabiltiy= [Expression 3]

the probability of the incident wave's being changed to the scattered wave =

$\langle \tilde{\psi}_f | V_1 | \psi_i \rangle|_1 = \tilde{T}_1(-\zeta_1^*) T_1(\alpha_1) \langle -\zeta_1^* | V_1 | \alpha_1 \rangle +$ $\tilde{T}_1(\zeta_1^*) T_1(-\alpha_1) \tilde{R}_1(\zeta_1^*) \tilde{\varphi}_1^{*2} \langle \zeta_1^* | V_1 | \alpha_1 \rangle +$ $\tilde{T}_1(-\zeta_1^*) T_1(\alpha_1) R_1(\alpha_1) \varphi_1^2 \langle -\zeta_1^* | V_1 | - \alpha_1 \rangle +$ $\tilde{T}_1(\zeta_1^*) T_1(-\alpha_1) R_1(-\alpha_1) \varphi_1^2 \tilde{R}_1(\zeta_1^*) \tilde{\varphi}_1^{*2} \langle \zeta_1^* | V_1 | - \alpha_1 \rangle$ where Wave field of incident wave at lth layer =

$\psi_i(\theta_0)|_1 = \prod_{j=1}^{l-1}(t_j\varphi_j)e^{ik_0\alpha_1 z_1} + \prod_{j=1}^{l-1}(t_j\varphi_j)R_1\varphi_1^2 e^{-ik_0\alpha_1 z_1}$ ( = ① + ② )

Wave field of scattered wave at lth layer $\tilde{\psi}_f(\theta_0)|_1 =$ $\prod_{j=1}^{l-1}(\tilde{t}_j^*\tilde{\varphi}_j^*)e^{-ik_0\zeta_1^* z_1} + \prod_{j=1}^{l-1}(\tilde{t}_j^*\tilde{\varphi}_j^*)\tilde{R}_1^*\tilde{\varphi}_1^{*2} e^{ik_0\zeta_1^* z_1}$ ( = ③ + ④ )

$T_1(\alpha_1) = \prod_{j=1}^{l-1}(t_j\varphi_j)$ $\tilde{T}_1(\zeta_1^*) = \prod_{j=1}^{l-1}(\tilde{t}_j^*\tilde{\varphi}_j^*)$ V=Potential due to the non-uniformity of the density In the transition probability above, the first term (I) of the right side represents the transition probability that corresponds to the case of FIG. 3A, the second term (II) thereof represents the transition probability that corresponds to the case of FIG. 3B, the third term (III) thereof represents the transition probability that corresponds to the case of FIG. 3C, and the fourth term (IV) thereof represents the transition probability that corresponds to the case of FIG. 3D, these terms being added together. Of course, they may provide a separate transition probability every term on the right side of the expression to thereby determine a transition probability according to each of the FIGS. 3A to 3D cases.

The transition probability shown above is the transition probability wherein the initial and final states, i.e. incoming and scattered waves are used as the exact solutions of the multilayer film. This transition probability is the one having taken thereinto the diffuse scattering phenomenon and multiple reflections occurring in the multilayer film. In the invention of the present application, the analysis is performed using the scattering function having introduced thereinto the forgoing transition probability.

For example, the expressions (I) to (IV) below represent the relationships each between the transition probability and the scattering function, each established according to a corresponding one of the FIGS. 3A to 3D cases in the film interior 1.

[Expression 4]

I: $|\langle -\zeta_1^* | V_1 | \alpha_1 \rangle|^2 = r_e^2 |F(q_1^+)|^2 \left( \dfrac{1 - e^{-2k_0 Im(\alpha_1 + \zeta_1) d_1}}{2k_o Im(\alpha_1 + \zeta_1)} \right)$ II: $|\tilde{\varphi}_1^{*2} \langle \zeta_1^* | V_1 | \alpha_1 \rangle|^2 =$ $r_e^2 |F(q_1^-)|^2 \left( e^{-4k_0 Im \zeta_1 d_1} \cdot \dfrac{1 - e^{-2k_0 Im(\alpha_1 - \zeta_1) d_1}}{2k_o Im(\alpha_1 - \zeta_1)} \right)$ III: $|\varphi_1^2 \langle -\zeta_1^* | V_1 | -\alpha_1 \rangle|^2 = r_e^2 |F(q_1^-)|^2 \left( e^{-4k_0 Im \alpha_1 d_1} \cdot \right.$ $\left. \dfrac{1 - e^{-2k_0 Im(\zeta_1 - \alpha_1) d_1}}{2k_o Im(\zeta_1 - \alpha_1)} \right)$ IV: $|\varphi_1^2 \tilde{\varphi}_1^{*2} \langle \zeta_1^* | V_1 | -\alpha_1 \rangle|^2 = r_e^2 |F(q_1^+)|^2 \left( e^{-4k_0 Im(\zeta + \alpha)_1 d_1} \cdot \right.$ -continued $$\left. \frac{e^{+2k_0 Im(\alpha_1 + \zeta_1)d_1} - 1}{2k_0 Im(\alpha_1 + \zeta_1)} \right)$$

where $q_l^+ = k_0 Re(\alpha_l + \zeta_l)$ $q_l^- = k_0 |Re(\alpha_l - \zeta_l)|$ $|F(q_1^+)|^2, |F(q_1^-)|^2$  [Expression 5]

... is the scattering function. Into this scattering function, there is substituted the scattering function I1 ($\theta$in, $\theta$out)(= $I_1(q), A \cdot I_1(q) \cdot S_1(q)$, etc.). By selecting various fitting parameter values in the scattering function I1 ($\theta$in, $\theta$out) that has been substituted, there is calculated a simulated scattering curve that will coincide with the actually measured scattering curve. The fitting parameter values at which the both curves coincide with each other represent the state of distribution of the particulate matter within the density-nonuniform multilayer film. By this, it is possible to highly accurately analyze in a simple way the state of distribution of the particulate matter, i.e. the non-uniformity of the density, based on the accurate consideration of the diffuse scattering phenomena and multiple reflections within the density-nonuniform multilayer film.

Figure 4:
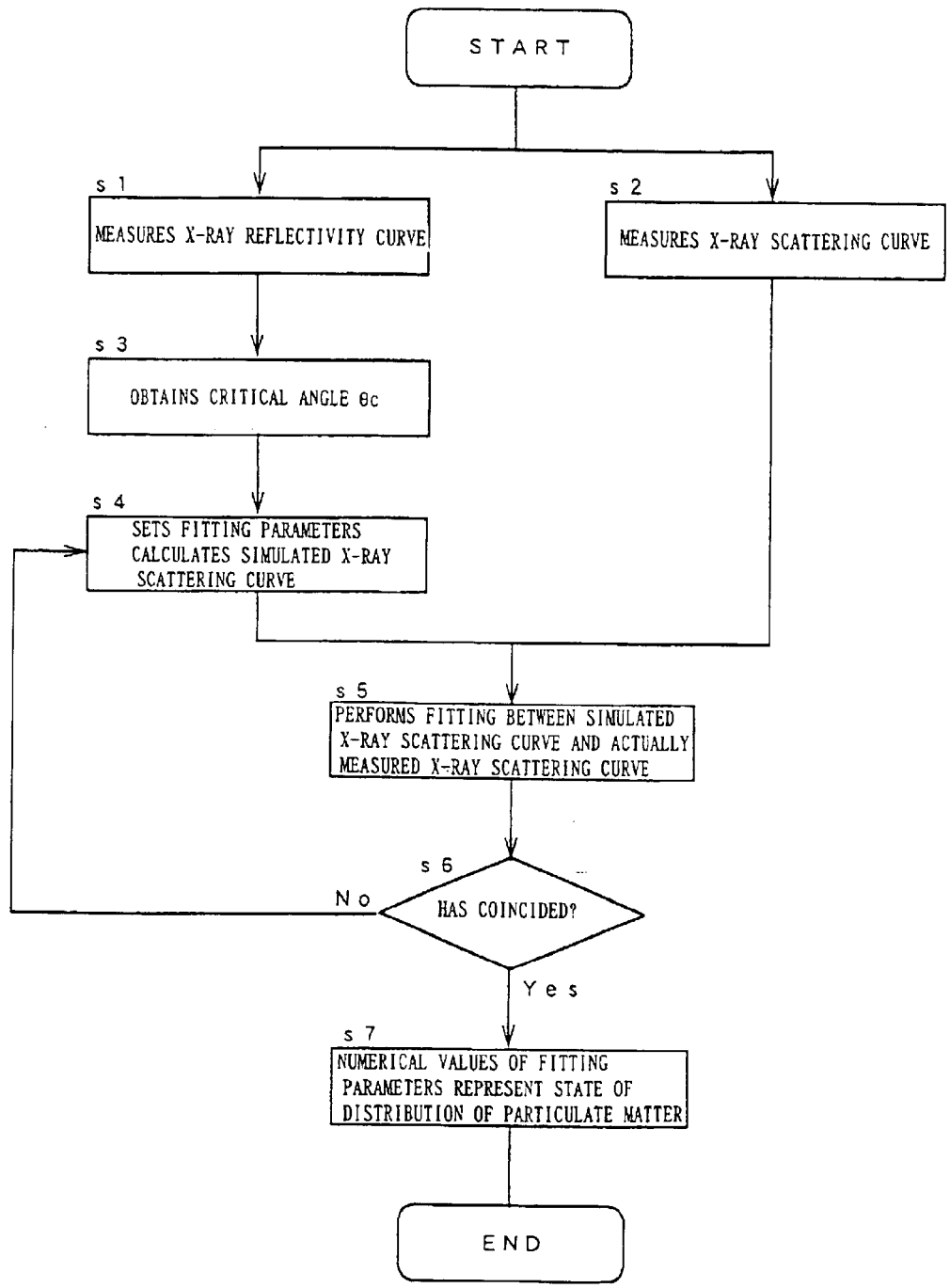
FIG. 4 is a flow chart illustrating a density-nonuniform multilayer film analyzing method according to the invention of the present application.

Hereinafter, the invention will more concretely be explained while referring to the respective analysis steps. FIG. 4 is a flow chart of that. It is to be noted that here an explanation will mainly be given of a case where using an X-ray.

<Steps s1 and s2> In the invention of the present application, simulation and fitting are performed using the scattering function that represents the X-ray scattering curve according to the fitting parameters that represents the distributed state of the particulate matter. However, in this task, there are needed X-ray reflectance curve, X-ray scattering curve, and various kinds of values that are derived from those curves. Therefore, first, as the pre-processing, measurement is performed of the X-ray reflectance curve and X-ray scattering curve regarding the density-nonuniform specimen having distributed therein particulate matter.

<Step s1> The X-ray reflectance curve is measured under the condition of the X-ray incident angle $\theta$in=the X-ray outgoing angle $\theta$out (i.e. under the condition of "the mirror surface reflection"). Here, the wording "X-ray incident angle $\theta$in" means an X-ray angle of incidence upon the specimen surface and the wording "X-ray outgoing angle $\theta$out" means an X-ray angle of outgoing with respect to the specimen surface.

<Step s2> The X-ray scattering curve is measured under the condition of, for example, the X-ray incident angle $\theta$in=the X-ray outgoing angle $\theta$out−the offset $\Delta\omega$, or, the X-ray incident angle $\theta$in=the X-ray outgoing angle $\theta$out+the offset $\Delta\omega$, or under both of these conditions (hereinafter they are referred to collectively as "$\theta$in=$\theta$out±$\Delta\omega$"). Here, the offset $\Delta\omega$ represents the angular difference between the $\theta$in=and the $\theta$out. In the case where $\Delta\omega$=0°, $\theta$in=$\theta$out. In this case, the reflection is the mirror reflection, and the measurement of the relevant curve results in the measurement the same as that made when the X-ray reflectance is measured. Measurement of the X-ray scattering curve is performed under the condition wherein that $\Delta\omega$ has gotten slightly deviated (offset) from 0°. Preferably, the $\Delta\omega$ is a numerical value that is as approximate to 0° as possible and that is as less affected as possible by the intense mirror surface reflection which occurs when $\Delta\omega$=0°.

Measurement of the X-ray scattering curve under $\theta$in=$\theta$out±$\Delta\omega$ is, in other words, measurement of the diffuse scattering. And this diffuse scattering is due to the existence of the particulate matter, namely the non-uniformity of the density of the density-nonuniform specimen. Therefore, by performing fitting between this actually measured X-ray scattering curve and a simulated scattering curve that is calculated using various kinds of functions as later described, it is possible to perform accurate analysis of the non-uniformity of the density of the density-nonuniform specimen.

Also, the X-ray scattering curve may be measured under the condition of scanning the X-ray outgoing angle $\theta$out with the X-ray incident angle $\theta$in being kept fixed, or under the condition of, conversely thereto, scanning the X-ray incident angle $\theta$in with the X-ray outgoing angle $\theta$out being kept fixed. In this case as well, it is possible to perform accurate measurement of diffuse scattering necessary for high-accuracy simulation and fitting.

<Step s3> Since in the scattering function as later described there are used the indexes of refraction $n_l$ (the angles of refraction $\alpha_l, \zeta_l$) of the density-nonuniform specimen in the film interior I, there are determined beforehand the indexes of refraction $n_l$ (the angles of refraction $\alpha_l, \zeta_l$) from the X-ray reflectance curve that has been measured. Determining the indexes of refraction $n_l$ (the angles of refraction $\alpha_l, \zeta_l$) from the X-ray reflectance curve can be performed using a known method. Concretely, the angle at which in the X-ray reflectance curve the reflectance (the intensity of the reflected X-ray) rapidly decreases is the critical angle $\theta$c. Among the critical angle $\theta c_1$, the numerical value $\delta_1$, and the refractive index $n_1$, there are the relationships of $\theta c_1 = \sqrt{(2\delta_1)}$ and $n_l = 1 - \delta_l$.

On the other hand, if there is known the element that constitutes each of the layers, it is also possible to determine the average density $\rho_l$ in each layer from the $\delta_l$. More specifically, if there are known the composition ratio $cj_l$, mass number $Mj_l$, and atomic scattering factor $fj_l$ of the constituent element $j_l$, the average density $\rho$ in each layer is determined using the following expression. Of course, the density of the density-nonuniform layer can also be known.

$$\delta_1 = \frac{r_e}{2\pi}\lambda^2 N_A \cdot \rho_1 \cdot \frac{\sum_j c_{j_1} Re(f_{j_1})}{\sum_j c_{j_1} M_{j_1}}$$  [Expression 6]

$r_e$: Classical electron radius≅2.818×10$^{-13}$ cm
$N_A$: Avogadro's number≅6.022×10$^{23}$ mol$^{-1}$
$\rho_l$: Average density of lth layer
$c_{jl}$: Composition ratio of the element j of lth layer
$M_{jl}$: Atomic weight of the element j of lth layer
$f_{jl}$: Atomic scattering factor of the element j of lth layer Each of the respective numerical values necessary for calculation can be predicted when producing the density-nonuniform specimen. The average density $\rho$ in this density-nonuniform specimen, together with the distributed state of the particulate matter, such as the particle diameters of the particles and the spread thereof within the density-nonuniform specimen, which will be determined in a way as later described, is the information that is very effective when evaluating and producing that density-nonuniform specimen.

<Step s4> Now, in the invention of the present application, after finishing the pre-processing for performance of the simulation and fitting in the above-described way, by using the scattering function that represents the X-ray scattering curve according to the fitting parameters that represent the distributed state of the particulate matter, arbitrary selection is performed of the numerical value of fitting parameter and then calculation is performed of the simulated X-ray scattering curve under the same condition ($\theta$in=$\theta$out±$\Delta\omega$ under $\theta$out being scanned with $\theta$in being fixed or under $\theta$in being scanned with $\theta$out being fixed) as that under which the scattering curve is measured.

More specifically, first, the following expression 7 is an example of the scattering function, which represents the X-ray scattering curve which can be used with respect to all, but the one corresponding to the mirror reflection $\theta$in=$\theta$out, of the values that each of the $\theta$in and $\theta$out can take.

$$I(\theta_{in}, \theta_{out}) = \int |F_s(q;\{p\})|^2 P(\{p\}) d\{p\} \qquad \text{[Expression 7]}$$

$I(\theta_{in}, \theta_{out})$: Scattering function
$F_s(q; \{p\})$: Form factor of scatter
$q=|q|$: Magnitude of the scattering vector
$q$: Scattering vector
$\theta_c=\sqrt{2\delta}$: Critical angle
$n=1-\delta$: Refractive index
$\lambda$: Wavelength of the X-rays
$P(\{p\})$: Distribution function of scatter
$\{p\}$: Set of the parameters of the distribution function In the scattering function that is given as the expression 7 above, form factor of scatter is an important element that determines the X-ray scattering curve. The wording "form factor of scatter" is one of the factors that each indicate a particular form model representing the form of, some particulate matter within the density-nonuniform specimen, which form models are distributed in some state with that specimen. When using this factor, it is possible to accurately grasp the effect resulting from the distribution of the particulate matter and, according to that factor, it is possible to simulate the X-ray scattering curve, which accurately reflects that effect, with a high degree of freedom and a high accuracy. It is to be noted that the $\{p\}$ which determines the distribution function of scatter means that several sets of parameters that can determine a corresponding number of distribution functions may exist.

Figure 5:
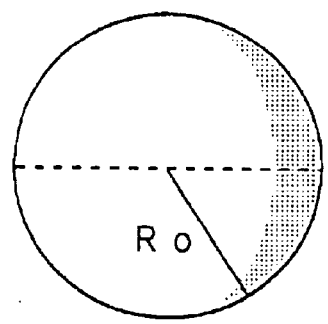
FIGS. 5A and 5B are views illustrating a spherical type model and circular-cylindrical model in a density-nonuniform form factor.
Figure 5:
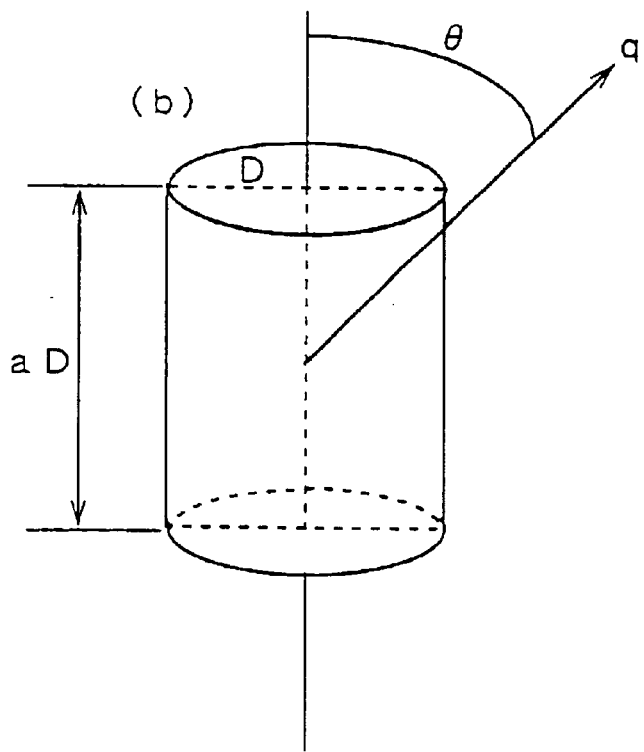

As the form model of the particulate matter, for example, a spherical type model that is exemplified in FIG. 5A and a circular cylindrical type model exemplified in FIG. 5B can be considered to exist. By arbitrarily selecting one of those models according to the object that is to be analyzed, the configuration of every type of particulate matter can be modeled.

First, the scattering function I(q) that uses the spherical type model is given, for example, as the following expression 8, the particle diameter distribution function that represents the particle diameter distribution in that expression 8 is given as the expression 9, and the particle form factor that represents the form of a certain type of particulate matter is given as the expression 10. It is to be noted that the expression 8 can be developed as in the following expression 11 for example, with the use of the expressions 9 and 10. In this case, the parameters [Ro, M] that represent the average particle diameter and distribution spread of the particulate matter that has been modeled by the spherical type model are the fitting parameters that represent the distributed state of particulate matter. The scattering functions I(q) of the expressions 8 and 11, according to those fitting parameters, namely by arbitrarily selecting the numerical values of the [Ro, M], can express various states of distribution. That is to say, those scattering functions I(q) express various X-ray scattering curves that are affected by such states of distribution.

$$I(q) = \int_0^\infty dR \cdot |\Omega^{FT}(q, R)|^2 \cdot P_{R_o}^M(R) \cdot \frac{1}{R^3} R_o^3 \rho_o \qquad \text{[Expression 8]}$$

$P_{R_o}^M(R)$: Distribution function of particle diameter
$R_o$: Average particle diameter parameter
$M$: Distribution spread parameter
$R$: Integrating variable
$q=|q|$: Magnitude of the scattering vector
$q$: Scattering vector
$\rho_o$: Average density of the particulate matter
$\Omega^{FT}(q, R)$: Form factor of particle $$P_{R_o}^M(R) = \frac{\left(\frac{M}{R_o}\right)^M}{\Gamma(M)} \cdot e^{-\frac{MR}{R_o}} \cdot R^{M-1} \qquad \text{[Expression 9]}$$

$\Gamma(M)$: $\Gamma$ function $$\Omega^{FT}(q, R) = \frac{4\pi R^3}{(q \cdot R)^3}[\sin(q \cdot R) - (q \cdot R) \cdot \cos(q \cdot R)] \qquad \text{[Expression 10]}$$

$$I(q) = \frac{8\pi^2 \left(1 + \frac{4q^2 R_o^2}{M^2}\right)^{-\frac{1+M}{2}}}{(-3+M)(-2+M)(-1+M)q^6} \qquad \text{[Expression 11]}$$

$$\left\{ \begin{array}{l} M^3\left(1 + \frac{4q^2 R_o^2}{M^2}\right)\left[\left(1 + \frac{4q^2 R_o^2}{M^2}\right)^{-\frac{3+M}{2}} - \cos\left[(-3+M)\tan^{-1}\left(\frac{2qR_o}{M}\right)\right]\right] + \\ (-3+M)(-2+M)M \cdot q^2 \cdot R_o^2\left[\left(1 + \frac{4q^2 R_o^2}{M^2}\right)^{-\frac{1+M}{2}} + \cos\left[(-1+M)\tan^{-1}\left(\frac{2qR_o}{M}\right)\right]\right] - \\ 2(-3+M)M^2 \cdot q \cdot R_o\left(1 + \frac{4q^2 R_o^2}{M^2}\right)^{\frac{1}{2}} \sin\left[(-2+M)\tan^{-1}\left(\frac{2qR_o}{M}\right)\right] \end{array} \right\}$$

While the mathematical expression 9 above corresponds to a case where the gamma distribution is represented as the particle diameter distribution, of course a particle diameter distribution function that represents a particle diameter distribution (such as a Gauss distribution) other than the gamma distribution may needless to say be employed. Namely, it is preferable to arbitrarily select the particle diameter distribution so that high-accuracy fitting may be realized between the simulated scattering curve and the actually measured scattering curve.

Next, an explanation will be given of the scattering function I(q) that uses the circular-cylindrical type model, which is for example given as the following expression 12. In this case, the parameters [D, a] that represent the particle diameter and aspect ratio of the particulate matter that has been modeled by the circular-cylindrical type model, together with the distribution spread parameter [M], are the fitting parameters that represent the state of distribution of the particulate matter. The scattering function I(q) of the expression 12 serves as the function that represents the X-ray scattering curve and that is affected by such various states of distribution by arbitrarily selecting the numerical values of the [D, a, M].

[Expression 12]

$$I(q) = \frac{2\pi^2 \rho_o}{q^6}\left(\frac{qD_o}{2}\right)^3 \cdot \frac{\left(\frac{M}{qD_o}\right)^M}{\Gamma(M)} \cdot$$

$$F(a, qD) = \int_0^\infty dx \cdot x^{M+2} F(a,x) e^{-\frac{M}{qD_o}x}$$

$$\int_0^\pi \sin\theta\, d\theta \left| \frac{\sin\left(\frac{a \cdot qD}{2} \cdot \cos\theta\right) J_1\left(\frac{qD}{2} \cdot \sin\theta\right)}{\left(\frac{qD}{2}\right)^2 \sin\theta\cos\theta} \right|^2$$

D: Diameter parameter
a: Aspect ratio parameter
M: Distribution spread parameter
q: Scattering vector
Γ(M): Γ function
$J_n(z)$: Bessel function Also, regarding the scattering vector q used in each of the respective expressions, it is necessary to use the scattering vector having considered with respect thereto the effect of refraction due to the particulate matter, which is shown in the following expression 13. When the specimen is in a state of its being a thin film, the effect of refraction of the incident X-rays upon the surface of that specimen importantly affects the measured scattering curve. Therefore, performing simulation based on the consideration of that refraction effect becomes necessary for realizing the high-accuracy density-nonuniform analysis. On this account, in the invention of the present application, using the scattering vector q that is given as the following expression 13 that accurately considers the refraction effect such as that given as the expression 4, the relevant scattering function is used as an optimum scattering function to simulation.

[Expression 13]
$$\begin{cases} q_1^+ = k_0 Re(\alpha_1 + \zeta_1) \\ q_1^- = k_0 |Re(\alpha_1 - \zeta_1)| \end{cases}$$

The refractive index $n_I$ and refracting angles $\alpha_I$, $\zeta_I$ that have been obtained from the X-ray reflection curve are utilized in this scattering vector q.

As described above, the scattering function that is based on arbitrarily selecting the expressions 8 to 11 or the expression 12, by accurately considering the effects due to the particulate matter, provides as simulated curves various scattering curves that are determined according to the fitting parameters that include the average particle diameter parameter Ro, distribution spread parameter M, diameter parameter D, and aspect ratio parameter a. Accordingly, by optimizing the numerical values of the respective parameters [Ro, M] or [D, a, M] as later described, it is possible to calculate a simulated scattering curve that coincides with the actually measured scattering curve to a very great extent.

Incidentally, it is a matter of course, in the expression 7, to give consideration to the structure factor of the atoms that constitute the particulate matter. In addition, in the expressions 7 to 12, strictly saying, not the scattering vector q but its magnitude |q| is used. The reason for this is that, while in general the relevant expression has used therein the vector q, in each of the respective expressions above it has been assumed that the particulate matter has random azimuths, thereby it has been assumed that measurement be made with isotropy (measured results don't depend on the directions).

A further explanation will be given of calculating the simulated X-ray scattering curve by using the scattering function. First, the conditions are set to the ones the same as those that exist when actually measuring the scattering curves. Then, if having selectively used the scattering function (the expressions 8 to 11) according to the spherical type model, the numerical values of the average particle diameter parameter Ro and distribution-spread parameter M are arbitrarily selected, while, if having selectively used the scattering function (the expression 12) according to the circular-cylindrical type model, the numerical values of the diameter parameter D, aspect ratio parameter a, and distribution-spread parameter M are arbitrarily selected. By using the expression 13, there is calculated the X-ray scattering curve in which there are used the selected values [Ro, M] or [D, a, M] under the condition of θin=θout±Δω under θout being scanned with θin being fixed or under θin being scanned with θout being fixed.

More specifically, the various kinds of parameters necessary for this calculation are Ro, M, D, a, q, θin, θout, δ, λ, and ρo as seen from the expressions 7 to 12 above. Of these parameters, δ and ρo are obtained from the reflectance curve, q can be calculated from θin, θout, δ, λ, and Ro, M, D, a are the fitting parameters. Accordingly, when performing simulation, merely by measuring the reflectance curve, and only if, thereafter, calculating the scattering function, it is possible to obtain a simulated X-ray scattering curve simply in a short period of time.

By the way, since the distribution of the particulate matter greatly affects the scattering curve obtained from the density-nonuniform specimen, the scattering function given as the expression 7 is made the one wherein the effects due to the scattering vector, density-nonuniform scattering form factor, etc. are taken into consideration. By doing so, obtaining a high-accuracy simulated scattering curve is realized. Also, the radiation area where an X-ray has entered the interior of the specimen and the state of correlation between two pieces of the particulate matter are also the factors that have effect upon the scattering curve.

In view of the above, in the invention of the present application, it aims to realize more accurate fitting and more enhance the analysis precision by taking into consideration the above-described various effects that result from the density-nonuniform specimen. To this end, as the above-described scattering function, there may be used the one wherein, for example, the "radiation area correction" and "particulate matter correlation function" have been introduced. The scattering function in this case is given, for example, as the following expression.

$$I(\theta_{in},\theta_{out})=A \cdot I(q) \cdot S(q) \qquad \text{[Expression 14]}$$

$I(\theta_{in},\theta_{out})$: Scattering function
$q=|q|$: Magnitude of the scattering vector
$q$: Scattering vector
$\theta_c=\sqrt{2\delta}$: Critical angle
$n=1-\delta$: Refractive index
$\lambda$: Wavelength of the X-ray In the scattering function above, the A represents the corrected radiation area and the S(q) represents the particulate matter correlation function. In this case as well, of course, the function according to the above-described spherical type model and that according to the circular-cylindrical type model can arbitrarily be selected as the I(q).

The radiation area correction A is given, for example, as the following expression.

$$A_1 = \frac{1}{\sin\theta_{in}} \qquad \text{[Expression 15]}$$

Also, the particulate matter correlation function S(q) is a function that represents the correlation between two pieces of the particulate matter and that is given, for example, as the following function.

$$S(q) = 1 + \int dr(n(r) - n_o)e^{iqr} \qquad \text{[Expression 16]}$$

n(r): Number density distribution function of the particulate matter
$n_0$: Average number density of the particulate matter
q: Scattering vector
r: Space coordinate When actually performing simulation, in the particulate matter correlation function S(q) that is given as the expression 16, it is necessary that some suitable specific model capable of representing the state of distribution be used as the density distribution function n(r) of the particulate matter.

For example, as an example of the specific model, under the assumption of a case where the particulate matter is distributed in the way two pieces of particles thereof are located at a between-particle-nearest distance L and in a state having a correlation coefficient A, those L and are used as the fitting parameters. In this case, the particle matter correlation function S(q) is given, for example, as the following expression.

$$S(q) = \frac{1}{1 - C(q)} \qquad \text{[Expression 17]}$$

-continued $$C(q) = \frac{1}{(1-\eta)^4(q \cdot L)^3} \begin{bmatrix} (1+2\eta)^2\left(\frac{\sin(q \cdot L)-}{q \cdot L\cos(q \cdot L)}\right)- \\ 6\eta\left(1+\frac{\eta}{2}\right)^2\left(\begin{array}{c}2\sin(q \cdot L)- \\ q \cdot L\cos(q \cdot L)- \\ \frac{2(1-\cos(q \cdot L))}{q \cdot L}\end{array}\right)+ \\ \frac{1}{2}\eta(1+2\eta)^2\left\{\begin{array}{c}\left(4-\frac{24}{(q \cdot L)^2}\right)\sin(q \cdot L)- \\ \left(q \cdot L-\frac{12}{q \cdot L}\right)\cos(q \cdot L)+ \\ \frac{24(1-\cos(q \cdot L))}{(q \cdot L)^3}\end{array}\right\} \end{bmatrix}$$

L: Distance of nearest neighbor of particle
$\eta$: Between-particle correlation coefficient (packing density) parameter In the case of the scattering function given as the expression 14, into which the particulate matter correlation function of that expression 17 has been incorporated, the various parameters necessary for calculating the simulated X-ray scattering curve are Ro, M, a, M, q ($\theta$in, $\theta$out, $\lambda$, $\delta$), $\rho$o, $\mu$, d, L, and $\eta$. Although the parameters that have been increased from the case of the above-described expression 7 are $\mu$, d, L, and $\eta$, the $\mu$ and d can be determined from the density-nonuniform multilayer film that is used for measurement. As in the case of the Ro, M, D, and a, the L and $\eta$ are the fitting parameters for performing fitting between the simulated scattering curve and the actually scattering curve, which represent the nearest distance and correlation coefficient between the particles of the particulate matter. Accordingly, only by measuring the X-ray reflectance curve, coordinating the respective numerical values of the average particle diameter parameter Ro, distribution spread parameter M, diameter D, aspect ratio parameter a, between-particle-nearest distance parameter L, and between-particle-correlation coefficient parameter $\eta$, and calculating the scattering function, a wider variety of X-ray scattering curves can readily be simulated.

Although since the derivation processes for obtaining the above-described scattering function, density-nonuniform scattering form factor, particle diameter distribution function, radiation area correction term, particulate matter correlation function each involve therein a number of steps they are omitted here, one feature of the invention of the present application resides in using for the scattering function for obtaining the X-ray scattering curves according to the above-described various kinds of fitting parameters for simulation of them. For example, if calculating the above-described respective mathematical expressions, it is possible to obtain simulated X-ray scattering curves necessary for analyzing the non-uniformity of the density.

Basically, each of the above-described mathematical expressions (the expressions 7 to 17) can be obtained by developing a known fundamental scattering function given as the following expression 18 using the following expressions 19 and 20 based on the consideration of the non-uniform distribution off the particulate matter.

$$\frac{d\sigma}{d\Omega} = \int \rho(r)'e^{-iqr'}dr' \int \rho(r)e^{iqr}dr \qquad \text{[Expression 18]}$$

$\rho(r)$: Distribution of electron density
q: Scattering vector r: Space coordinate $$\rho(r) = \sum_i \rho_i(r - R_i) \quad \text{[Expression 19]}$$

$R_i$: Position of a particulate matter i
$\rho_i(r-R_i)$: Electron density distribution in the particulate matter i $$\Omega^{FT}(q) = \int dr \langle \rho(r) \rangle e^{iqr} \quad \text{[Expression 20]}$$

$$\langle \rho(r) \rangle = \frac{\sum_i \rho_i(r)}{N}$$

$\Omega^{FT}(q)$: Particle form factor
$\langle \rho(r) \rangle$: Average electron density distribution of the particulate matter
N: Number of the particulate matter The N (the number of the particulate matter) in the expression 20 can be determined, for example, as in the following expression, from the object area to be analyzed of the density-nonuniform multilayer film.

$$N = \frac{S_o d}{\sin\theta_{in}} \cdot \frac{1 - e^{-\left(\frac{1}{\sin\theta'_{in}} + \frac{1}{\sin\theta'_{out}}\right)\mu d}}{\mu d \left(\frac{1}{\sin\theta'_{in}} + \frac{1}{\sin\theta'_{out}}\right)} \cdot \frac{1}{R_o^3} \quad \text{[Expression 21]}$$

$$S_o = L_x L_y$$

d: Thickness of the sample
$S_o$: Footprint

Of course, the respective expressions shown above are merely illustrative and, needless to say, the variables names and terms arrangement used therein are not limited to those illustrated above.

For example, although the scattering functions given as the expressions 8 and 12 and the expressions 14 and 17 use [Ro, M] and [D, a, M] and [L, η] as the fitting parameters, other than this, for example, it is possible to use the scattering function representing the X-ray scattering curve according to the fitting parameters that represent the percentage content and correlation length of the particulate matter. In this case, the scattering functions are given, for example, as the following expressions 22 and 23.

$$I(\theta_{in}, \theta_{out}) = |\Omega^{FT}(q)|^2 \quad \text{[Expression 22]}$$

$I(\theta_{in}, \theta_{out})$: Scattering function
$\Omega^{FT}(q)$: Form factor of scatter
$q=|q|$: Magnitude of the scattering vector
q: Scattering vector
$\theta_c = \sqrt{2\delta}$: Critical angle
$n=1-\delta$: Refractive index
λ: Wavelength of the X-ray $$\Omega^{FT}(q) = (\Delta\rho)^2 \frac{8\pi P(1-P)\xi^3}{(1+q^2\xi^2)^2} \quad \text{[Expression 23]}$$

Δρ: Difference in density between the particulate matter and the other specimen-constituting substances
P: Percentage content parameter of the particulate matter
ξ: Correlation length parameter of the particulate matter In the case where the density-nonuniform specimen is a porous film and the particulate matter is fine particles or holes that form that porous film, in the expression 23 the Δρ represents the difference in density between the fine particles or holes and the other substances (not the substrate but the ones that constitute the film itself) that constitute the porous film, the P represents the fine particles percentage or holes percentage, and the ζ represents the correlation length of the fine particles or holes.

In the case using this scattering function, fitting between the simulated X-ray scattering curves and the actually measured X-ray scattering curve is performed while the P and ξ serving as the fitting parameters are each being changed.

Further, also, it is possible to use the following scattering function, too. When using an ordinary X-ray diffraction meter, regarding the angle-measuring direction=the rotational direction of the goniometer, measurement is possible with a high degree of parallelism but, regarding the orthogonal direction with respect thereto, measurement has a high degree of divergence. Since that degree of divergence has an effect upon the profile of the small angle scattering, correcting the slit length becomes necessary. In the case where having taken that slit length correction into consideration, when it is assumed that W(s) represents the slit function, the scattering function $I_{obs}(q)$ that is measured with respect to the scattering function I(q) is given as the following expression.

$$I_{obs}(q) = \int_{-\infty}^{\infty} I\left(\sqrt{q^2 + s^2}\right) W(s) ds \quad \text{[Expression 24]}$$

Figure 6:
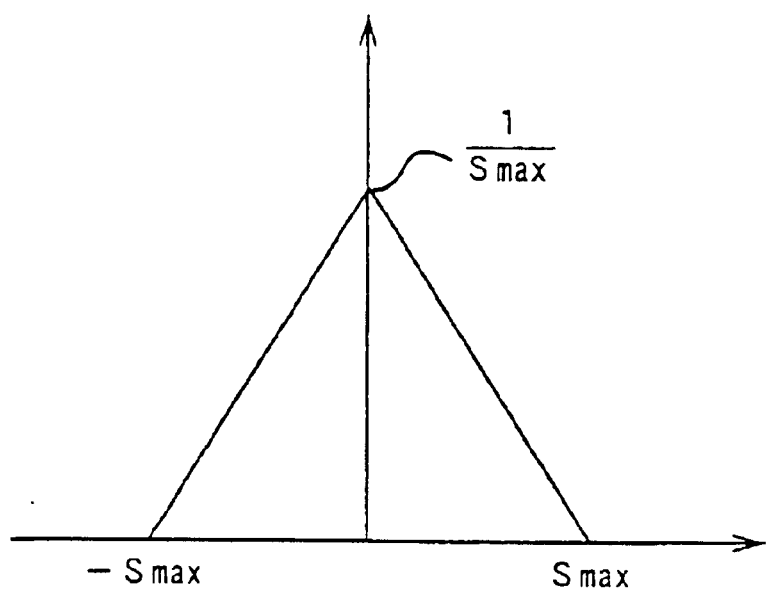
FIG. 6 is a view illustrating an example of the slit function.

Accordingly, each of the above-described respective scattering functions I(q) needs only to be replaced with the scattering function $I_{obs}(q)$ given as the expression 31. FIG. 6 is a view illustrating an example of the slit function W(s). Of course, this is merely one example, and the slit function W(s) must be suitably conformed to the X-ray diffraction meter.

As seen from the foregoing, the I(θin, θout)(=I(q), A·I(q) ·S(q), etc.) above is the fundamental expression of the scattering functions representing the X-ray scattering curves according to the fitting parameters that represent the distributed state of the particulate matter. However, in the invention of the present application, it is directed to analyzing the density-nonuniform multilayer film as the density-nonuniform specimen. In this view, for further enhancing the analysis accuracy by considering the diffuse scattering phenomena and multiple reflection phenomena occurring in the multilayer film, as described before, the invention attempts to substitute the scattering function I(θin, θout)(=I(q), A·I (q)·S(I), etc.) into the scattering function F(q) given in the expression 4. By doing so, the invention attempts to establish the scattering function into which there have been taken the diffuse scattering phenomena and multiple reflection phenomena in the multilayer film, the scattering function having also introduced thereinto the transition probabilities wherein the exact solutions of the multilayer film are set as the initial state and the final state. The invention attempts to finally use that scattering function.

While in the scattering function in this case the fitting parameters are as they are in each of the above-described functions I(θin, θout), the numerical values that have added thereto the known values in the expressions 1 to 3 used in the expression 4 are the ones that become further needed for calculation of the simulated X-ray scattering curves. Since these numerical values can be determined by prediction when producing the density-nonuniform multilayer film that is to be analyzed, all other of them than the fitting parameters is known quantities.

Meanwhile, the X-ray that enters the density-nonuniform multilayer film and advances through the multilayer film is scattered not only at the surface of the specimen but at the interface between each two of the films (including the interface between the substrate and the film). This interfacial scattering has its effects cumulatively increased as the number of the layers becomes increased. For this reason, considering also the interfacial scattering with respect to the above-established scattering function having introduced thereinto the transition probabilities enables getting more highly accurate simulated scattering curves and thereby enables more enhancing the accuracy of the analysis of the density-nonuniform multilayer film.

In view of this, in the invention of the present application, consideration is given to further introducing into the scattering function having introduced thereinto the transition probabilities the effects of both of the surface scattering due to the condition of the surface and the interfacial scattering due to the condition of the interface. In the S. K. Sinha, E. B. Sirota, and S. Garoff, "X-ray and neutron scattering from rough surfaces" Physical Review B, vol. 38, no. 4, pp. 2297–2311, August 1988, description is certainly made of the surface scattering. However, neither description nor implication is made of the interfacial scattering in the multilayer film specimen. By the studies and development made by the inventors of the invention of this application, for the first time, there has been realized the simulation made by the scattering function having simultaneously considered thereinto the surface/interfacial scattering such as that which will be explained below. Incidentally, in the invention of the present application, the wording "the interface (interfacial roughness/interfacial scattering)" is used to mean both of the "between-film interface" and the surface of the surface layer, i.e. "the interface between the outside of the specimen and the surface layer", and when indicating only the surface alone, in particular, of the surface layer, it is called "the specimen surface".

Figure 7:
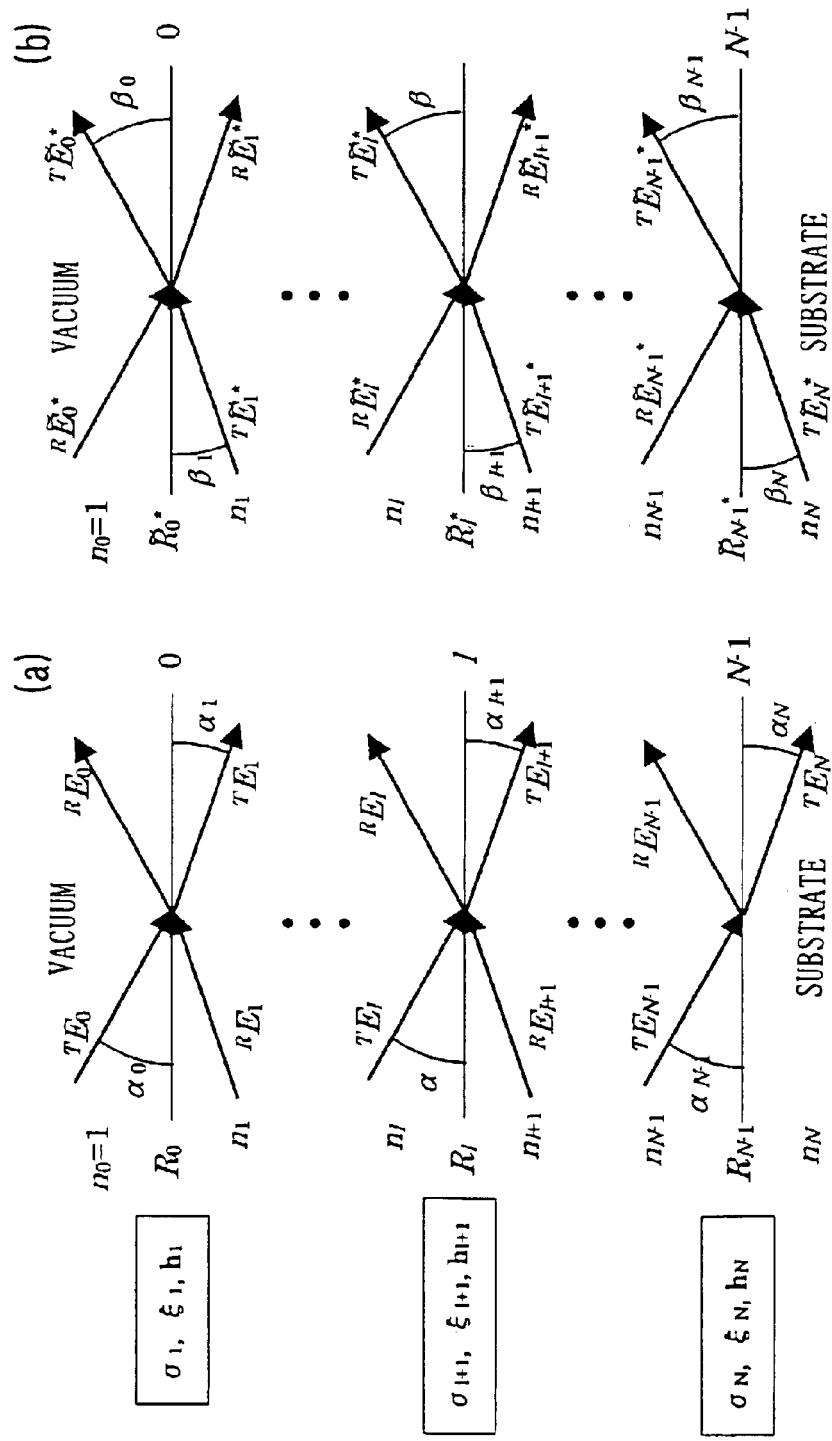
FIGS. 7A and 7B are schematic views each illustrating what the electric field within a density-nonuniform multilayer film having a multilayer structure the number of whose layers is N is alike.

Each of FIGS. 7A and 7B illustrates the behavior of the electric field within a thin film having a multilayer structure the number of whose layers is N. The view taken in each of them is almost the same as that taken in each of FIGS. 1 and 2. The incident angle of the incident wave is indicated by a and the outgoing angle of the scattered wave is indicated by β. Here, $^TE_l$ and $^RE_l$ respectively represent the traveling wave and the reflected wave in one layer. If the refractive index $n_l$, thickness $d_l$, and X-ray incident angle $\alpha_o$ of each layer are known, those field values can be calculated according to the Fresnel's formulas.

Regarding the scattered wave, it is necessary to consider about the wave that is produced within the film and goes out at the outgoing angle $\beta_o$ from the specimen surface. As the solution of the wave equation representing the electric field within the multilayer film that satisfies that condition, there is the one obtained by performing time reversal on the ordinary solution. This solution is obtained by deriving a complex conjugate from the ordinary solution and further performing substitution like t→−t (k→−k). The resulting solutions are represented by the $^TE_l$ and $^RE_l$ having added thereto the tilde "~" and the complex conjugate "*", provided, however, that, at this time, the waves that go out from the specimen surface are $^TE_o$'s having added thereto "~" and "*".

First, the electric fields $^TE_l$ and $^RE_l$ produced due to the incident wave (see FIG. 7A), specifically, can be written as the following expressions.

[Expression 25]

$$^TE_1(z_1) = \prod_{j=1}^{l-1}(t_j\varphi_j)e^{ik_0\eta_1 z_1}$$

$$^RE_1(z_1) = \prod_{j=1}^{l-1}(t_j\varphi_j)(R_1\varphi_1^2)e^{-ik_0\eta_1 z_1}$$

where
$E_l$=Strength of wave field in each layer $$k_0 = \frac{2\pi}{\lambda} = \begin{array}{l}\text{Wave vector of the incident wave}\\ \text{upon the sample surface (known value)}\end{array}$$

$\lambda$=Wavelength of the incident wave=the wavelength of the outgoing wave (known value)
$\eta_l=\sqrt{n_1-\cos^2\alpha_0}$
$n_1$=Refractive index of each layer (known value)
$\alpha_0$=Incident angle to the specimen surface (known value)
$d_l=z_l$=Depth from each interface (known value)
$\phi_l=e^{ik_0\eta_l\cdot d_l}$=Phase factor when the wave propagates through each layer (known value)

$$t_1 = \frac{1-\gamma_1 R_1}{\tau_1} = \begin{array}{l}\text{Transmitted coefficient at each interface}\\\text{each layer (known value)}\end{array}$$

$$\left\{R_N = 0, R_{N-1} = \gamma_{N-1}, \cdots, R_1 = \frac{R_{l+1}\varphi_{l+1}^2+\gamma_1}{R_{l+1}\varphi_{l+1}^2+\gamma_1+1}, R_0 = \frac{R_1\varphi_1^2+\gamma_0}{R_1\varphi_1^2+\gamma_0+1}\right\}$$

= Reflection coefficient at each interface (known value)

$$\gamma_1 = \frac{\eta_1-\eta_{l+1}}{\eta_1+\eta_{l+1}} = \text{Frenell's coefficient at each interface (known value)}$$

$$\tau_1 = \frac{2\eta_{l+1}}{\eta_l+\eta_{l+1}}$$

l=Layer number 0 . . . N

Also, regarding the electric fields TE1 and RE1 added with "~" and "*", as well, produced due to the scattered waves (see FIG. 7B), similarly, they can be written as the following expressions.

[Expression 26]

$$^T\tilde{E}_l^*(z_l) = \prod_{j=1}^{l-1}(\tilde{t}_j^*\tilde{\varphi}_j^*)e^{-ik_0\zeta_l z_l}$$

$$^R\tilde{E}_l^*(z_l) = \prod_{j=1}^{l-1}(\tilde{t}_j^*\tilde{\varphi}_j^*)(\tilde{R}_l^*\tilde{\varphi}_l^{*2})e^{ik_0\zeta_l z_l}$$

where
$E_l$=Strength of wave field in each layer $$k_0 = \frac{2\pi}{\lambda}$$
= Wave vector of the scattered wave from the sample surface
(known value)

$\lambda$=Wavelength of the scattered wave=the wavelength of the incident wave (known value)
$\zeta_l=\sqrt{n_1-\cos^2\beta_0}$=Refractive index of each layer (known value)
$\beta_0$=Exit angle to the sample surface (known value)
$\phi_l^*=e^{-ik_0\zeta_l\cdot d_l}$=Phase factor when the wave propagates through each layer (known value)

$d_l = Z_l$ = Depth from each interface (known value)

$$\tilde{t}_l^* = \frac{1 - \tilde{\gamma}_l^* \tilde{R}_l^*}{\tilde{\tau}_l^*}$$

= Transmitted coefficient of each interface (known value)

$$\tilde{R}_l^* = \frac{\tilde{R}_{l+1}^* \tilde{\varphi}_{l+1}^{*2} + \tilde{\gamma}_l^*}{\tilde{R}_{l+1}^* \tilde{\varphi}_{l+1}^{*2} \tilde{\gamma}_l^* + 1}$$

$$\left\{ \tilde{R}_N^* = 0, \tilde{R}_{N-1}^* = \tilde{\gamma}_{N-1}^*, \ldots, \tilde{R}_l^* = \frac{\tilde{R}_{l+1}^* \tilde{\varphi}_{l+1}^{*2} + \tilde{\gamma}_l^*}{\tilde{R}_{l+1}^* \tilde{\varphi}_{l+1}^{*2} \tilde{\gamma}_l^* + 1}, \tilde{R}_0^* = \frac{\tilde{R}_1^* \tilde{\varphi}_1^{*2} + \tilde{\gamma}_0^*}{\tilde{R}_1^* \tilde{\varphi}_1^{*2} \tilde{\gamma}_0^* + 1} \right\}$$

= Reflection coefficient at each interface (known value)

$$\tilde{\gamma}_l^* = \frac{\zeta_l^* - \zeta_{l+1}^*}{\zeta_l^* + \zeta_{l+1}^*}$$

= Reflection coefficient (Frenell's coefficient) (known value)

$$\tilde{\tau}_l^* = \frac{2\zeta_{l+1}^*}{\zeta_l^* + \zeta_{l+1}^*}$$

l = Layer number 0 . . . N

These expressions 25 and 26 can be calculated if the incident angle and outgoing angle and the parameters $n_l$ and $d_l$ of the film structure are known.

Using these expressions, the transition probability from the incident wave to the scattered wave that is calculated using the potential W1 due to the roughness at the interface 1-1, i.e. the interfacial roughness, can be written as the following expressions 27 and 28.

Wave field of incident wave at $l$th layer = [Expression 27]

$$\psi_i(\alpha)\big|_l = \prod_{j=1}^{l-1}(t_j \varphi_j) + \prod_{j=1}^{l-1}(t_j \varphi_j)(R_l \varphi_l^2)$$

$$= T_l + T_l R_l \varphi_l^2$$

Wave field of scattered wave at $l$th layer =

$$\tilde{\psi}_f(\varphi)\big|_l = \prod_{j=1}^{l-1}(\tilde{t}_j^* \tilde{\varphi}_j^*) + \prod_{j=1}^{l-1}(\tilde{t}_j^* \tilde{\varphi}_j^*)(\tilde{R}_l^* \tilde{\varphi}_l^{*2})$$

$$= \tilde{T}_l^* + \tilde{T}_l^* \tilde{R}_l^* \tilde{\varphi}_l^{*2}$$

Amplitude of transition probability = [Expression 28]

$$\langle \tilde{\psi}_i(\alpha) | W_l | \psi_f(\beta) \rangle = \tilde{T}_l T_l \langle -\zeta_l^* | W_l | \eta_l \rangle +$$
$$\tilde{T}_l \tilde{R}_l \tilde{\varphi}_l^2 T_l \langle \zeta_l^* | W_l | \eta_l \rangle +$$
$$\tilde{T}_l T_l R_l \varphi_l^2 \langle -\zeta_l^* | W_l | -\eta_l \rangle +$$
$$\tilde{T}_l \tilde{R}_l \tilde{\varphi}_l^2 T_l R_l \varphi_l^2 \langle \zeta_l^* | W_l | -\eta_l \rangle$$

The square of the absolute value in the expression 28 represents the scattering strength. While calculating the square of the absolute value in the expression 28 is accompanied by the appearance of the cross term in the respective scattering process, the effect of that is considered as being small and, as at the time of the scattering (see the expression 3) due to the above-described within-film particulate matter, there is calculated the sum of the squares of the absolute values of the respective interfacial scatterings.

Figure 8:
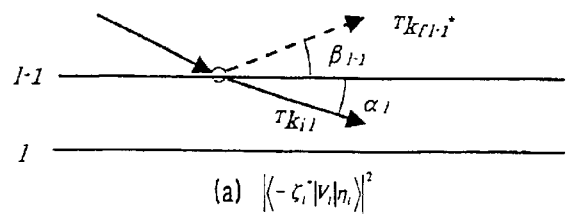
FIGS. 8A to 8D are schematic views illustrating various kinds of interfacial scattering phenomena.
Figure 8:
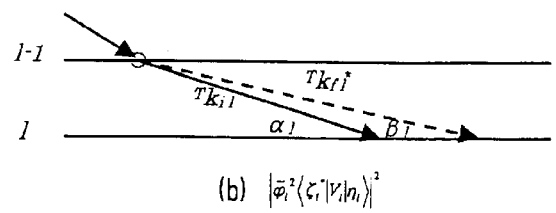
Figure 8:
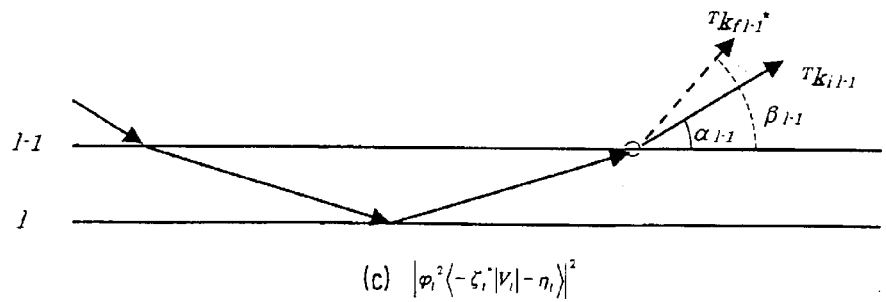
Figure 8:
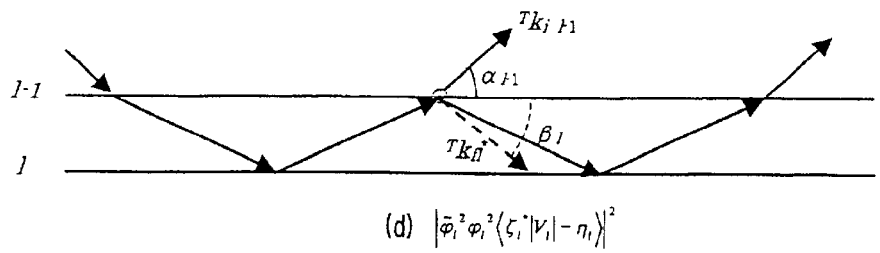

The following expressions 29(a) to 29(b) represent the squares of the absolute values of the respective interfacial scatterings illustrated in FIGS. 8A to 8D. FIG. 8A illustrates a state of the wave's being scattered at an arbitrary one interface 1-1; FIG. 8B illustrates a state of the wave's scattered by the upper layer interface 1-1 reaching the lower layer interface 1; FIG. 8C illustrates a state of the wave's reflected by the interface 1-1 of the lower layer being scattered by the interface 1-1 of the upper layer; and FIG. 8D illustrates a state of the wave's reflected by the interface 1 of the lower layer being scattered to the interface 1-1 of the upper layer and thereafter being again reflected by the interface 1 of the lower layer.

[Expression 29]

$$|\langle -\zeta_l^* | W_l | \eta_l \rangle|^2 = |P_l(q^+)|^2 \quad (a)$$
$$|\phi_l^2 \langle \zeta_l^* | W_l | \eta_l \rangle|^2 = |P_l(q^-)|^2 \exp[-4k_0 Im(\zeta_l) d_l] \quad (b)$$
$$|\phi_l^2 \langle -\zeta_l^* | W_l | -\eta_l \rangle|^2 = |P_l(q^-)|^2 \exp[-4k_0 Im(\eta_l) d_l] \quad (c)$$
$$|\phi_l^2 \phi_l^2 \langle \zeta_l^* | W_l | -\eta_l \rangle|^2 = |P_l(q^+)|^2 \exp[-4k_0 Im(\eta_l + \zeta_l) d_l] \quad (d)$$

In the expression 29 above, the Pl (q) represents the form factor that produces the potential Wl.

From the expressions 28 and 29, the scattering intensity is as in the following expression.

[Expression 30]

$$\text{Scattering intensity} = |\langle \tilde{\psi}_i(\alpha) | W_l | \psi_f(\beta) \rangle|^2 \sum_{l=1}^{N} |\tilde{T}_l T_l|^2 S(q_{zl}^+, q_r, \sigma_l, \xi_l, h_l) +$$

$$\sum_{l=1}^{N-1} \left( \begin{array}{c} |\tilde{T}_l \tilde{R}_l T_l|^2 \exp[-4k_0 \text{Im}(\zeta_l) d_l] + \\ |\tilde{T}_l T_l R_l|^2 \exp[-4k_0 \text{Im}(\eta_l) d_l] \end{array} \right) S(q_{zl}^-, q_r, \sigma_l, \xi_l, h_l) +$$

$$\sum_{l=1}^{N-1} |\tilde{T}_l \tilde{R}_l T_l R_l|^2 \exp[-4k_0 \text{Im}(\eta_l + \zeta_l) d_l] S(q_{zl}^+, q_r, \sigma_l, \xi_l, h_l)$$

where $$|P_l(q^+)|^2 = |\langle -\zeta_l^* | W_l | \eta_l \rangle|^2 = |\langle \zeta_l^* | W_l | -\eta_l \rangle|^2 = S(q_{zl}^+, q_r, \sigma_l, \xi_l, h_l)$$

$$|P_l(q^-)|^2 = |\langle \zeta_l^* | W_l | \eta_l \rangle|^2 = |\langle -\zeta_l^* | W_l | -\eta_l \rangle|^2 = S(q_{zl}^-, q_r, \sigma_l, \xi_l, h_l)$$

$$S(q_{zl}, q_r, \sigma_l, \xi_l, h_l) = \frac{|k_0^2 (n_{l-1}^2 - n_l^2)|^2 \exp\left[-(q_{zl}^2 + q_{zl}^{*2})\frac{\sigma_l^2}{2}\right]}{16\pi^2 |q_{zl}|^4} \cdot$$

$$\int_0^\infty r \left( \exp\left[|q_{zl}^2| \sigma_l^2 \exp\left[-\left(\frac{r}{|q_{zl}| \xi_l}\right)^{2h_l}\right]\right] - 1 \right) J_0\left(\frac{q_r}{q_{zl}}\right) dr$$

$q_{zl}^+ = k_0 \text{Re}(\eta_l + \zeta_l)$
$q_{zl}^- = k_0 |\text{Re}(\eta_l - \zeta_l)|$
$q_r = k_0 (\cos(\eta_0) - \cos(\zeta_0))$ In the expression 30 above, $\sigma_l$, $\delta_l$, and $h_l$ represent the roughness (roughness) parameter, lateral correlation length parameter, and Hurst parameter of the interface 1-1, respectively. Also, $J_o$ represents the 0th Bessel function.

The expression 30 that has been established as above is an example of the transition-probability-introduced scattering function having considered thereinto the interfacial scattering, and the roughness parameter $\sigma$, in-surface correlation length parameter $\delta$, and Hurst parameter h are the fitting parameters. By using the transition probability-introduced scattering function, such as that represented by the expression 30 above, having further introduced thereinto the fitting parameters capable of representing the interfacial conditions causing the occurrence of the interfacial scattering with a high degree of freedom and a high degree of accuracy, it becomes possible to calculate with a higher degree of accuracy the simulated scattering curve of the density-nonuniform multilayer film having also considered thereinto the interfacial scattering phenomena in each layer. As a result of this, it also becomes possible to easily and highly accurately analyze the interfacial condition as well as the state of distribution of the particulate matter.

<Step s5> After having calculated the simulated X-ray scattering curve by using the above-described transition probability-introduced scattering function, fitting is performed between the simulated X-ray scattering curve and the actually measured X-ray scattering curve. In the fitting operation, there is examined the degree of coincidence between the both curves (or the difference between the both curves). For example, the difference between the both curves can be determined as follows.

$$x^2 = \sum_i \left(\log I_i(exp) - \log I_i(cal)\right)^2 \quad \text{[Expression 31]}$$

$I_i(exp)$: Actually measured data of the (i)th measuring point $I_i(cal)$: Simulated data of the (i)th measuring point <Step s6> If that degree of coincidence (or difference) is a prescribed value or within a prescribed range, it is determined that the both curves coincide with each other. If otherwise, it is determined that the both curves don't coincide.

<Step s6 No→step s4→step s5> In the case where it is determined that the both curves don't coincide, the step of changing the fitting parameter representing the state of distribution of the particulate matter in the scattering function and the step of calculating the simulated X-ray scattering curve again are sequentially executed thereby determining the coincidence between that simulated X-ray scattering curve and the actually measured X-ray scattering curve. This process is repeatedly performed while coordinating and changing the numerical values of the fitting parameters until the both curves coincide. In the case where using the I(q) given as the expression 8 or 12 as the F(q) in the expression 4, the values [Ro, M] or [D, a] are changed, in the case where using the I (θin, θout) given as the expression 14 having incorporated thereinto the particulate matter correlation function S(q) of the expression 17 as that F(q), the values [L, η] are changed in addition to the values [Ro, M] or [D, a], and in the case where using the I (θin, θout) given as the expression 22 as that F(q), the values [P, ξ,] are changed. Also, in the case of the expression 30, the values [σ, ξ, h] are the objects with respect to which fitting is performed.

<Step s6 Yes→step s7> The selected values of the fitting parameters when the simulated X-ray scattering curve and the actually measured X-ray scattering curve have coincided with each other are the values that represent the state of distribution of the particulate matter within the density-nonuniform multilayer film that is the object to be analyzed. The numerical values of the fitting parameters [Ro, M] are the average particle diameter and distribution spread of the particulate matter, the numerical values of the fitting parameters [D, a, M] are the diameter, aspect ratio, and distribution spread of the particulate matter, the numerical values of the fitting parameters [L, η] are the between-particle-nearest length and correlation coefficient of the particulate matter, the numerical values of the fitting parameters [P, ξ] are the percentage content and correlation length of the particulate matter, and the numerical values of the fitting parameters [σ, ξ, h] are the roughness of the interface (including the specimen surface), in-surface correlation length, and Hurst parameter value.

Incidentally, in this fitting operation, for example, by using the non-linear least square, it is possible to determine the optimum values of the respective fitting parameters with a high efficiency.

By using the transition probability-introduced scattering function having considered thereinto the non-uniformity of the density in the multilayer film as stated above, the simulated X-ray scattering curve has increased very much the degree of coincidence thereof as viewed with respect to the actually measured scattering curve. In addition, the respective fitting parameters very accurately represent the state of distribution of the particulate matter in the actual multilayer film and hence can realize highly accurately representing the non-uniformity of the multilayer film.

Also, measurement that is made with respect to the density-nonuniform multilayer film is only reflectance measurement and scattering curve measurement alone. Therefore, there are no inconveniences that, as in the case of the conventional gas adsorption operation, measurement amount of time becomes great, or limitation is imposed on the kind of the thin film in terms of whether gas can be introduced into the thin film. Further, nor is it necessary that, as in the case of the conventional small angle scattering technique, for example, the thin film formed on the substrate be peeled off from the substrate. Accordingly, it is possible to realize, with respect to various kinds of density-nonuniform multilayer films, analysis of the non-uniformity of the density, on a non-destruction basis and in a short time.

Incidentally, the foregoing is an explanation given, mainly, of the case where an X-ray is used. However, even in the case where using a corpuscular ray such as a neutron ray and electron ray, also, it is needless to say possible to analyze the state of distribution of the particulate matter within the density-nonuniform multilayer film and the average density in that film. The scattering function referred to as above can also be applied with respect to the reflectance curve and scattering curve of the corpuscular ray as is (the foregoing description needs only to be read by replacing the "X-ray" with the "corpuscular ray"). Namely, there can be realized a very high accuracy of coincidence between the simulated corpuscular-ray scattering curve and the actually measured corpuscular-ray scattering curve, thereby a high-accuracy of analysis of the non-uniformity of the density can be realized.

In the above-described density-nonuniform multilayer film analyzing method according to the invention of the present application, calculation steps such as simulation and fitting can be executed using a computer such as a general-purpose computer and a computer for analysis only.

Figure 9:
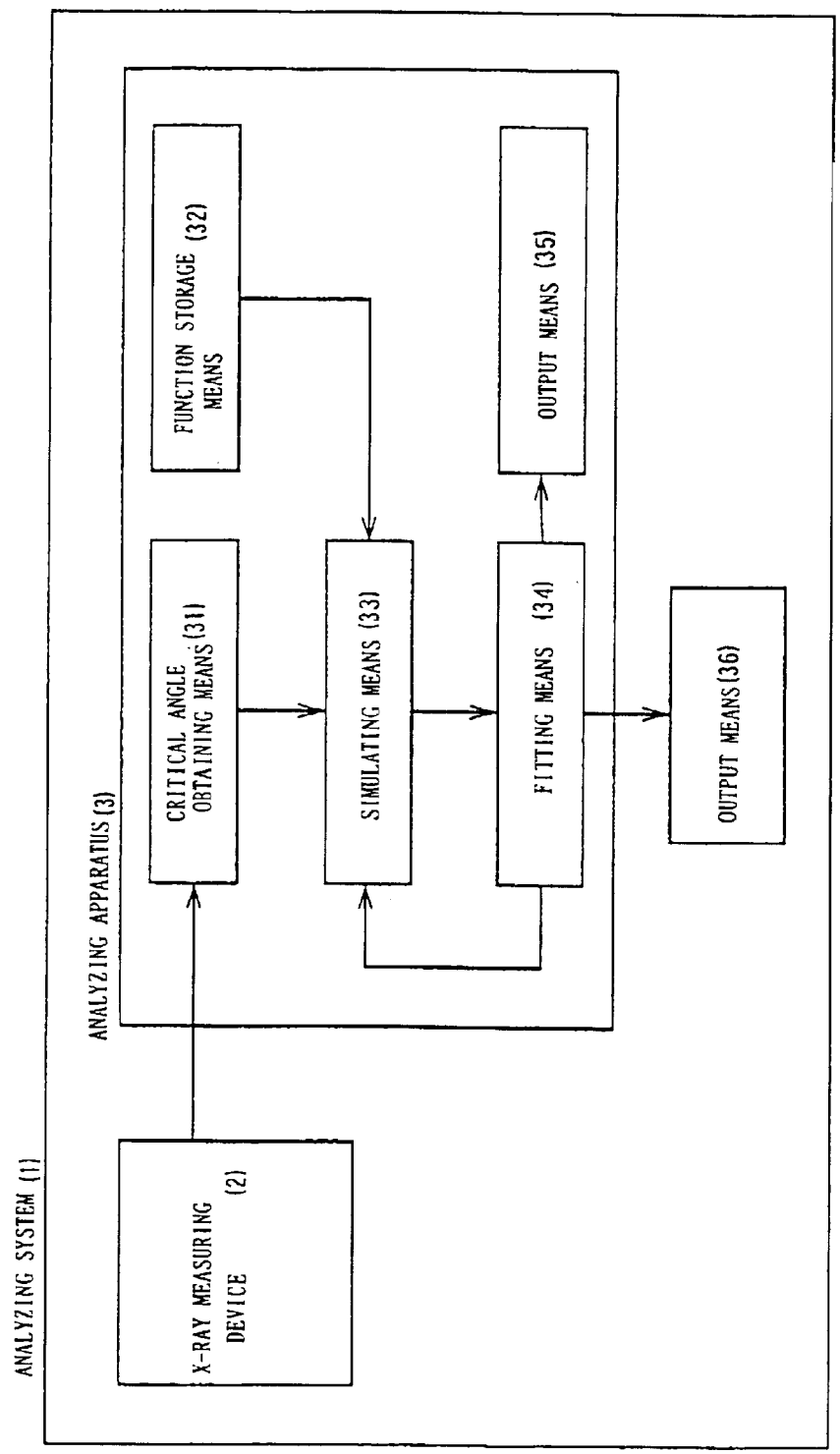
FIG. 9 is a functional block diagram illustrating a density-nonuniform multilayer film analyzing apparatus and system according to the invention of the present application.

FIG. 9 is a functional block diagram illustrating one form of density-nonuniform multilayer film analyzing apparatus and analyzing system that executes that density-nonuniform multilayer film analyzing method. This density-nonuniform multilayer film analyzing system (1) is the one where an X-ray is used, and includes an X-ray measuring device (2) and density-nonuniform multilayer film analyzing apparatus (3).

The X-ray measuring device (2) is for measuring the X-ray reflectance curve and X-ray scattering curve of the density-nonuniform multilayer film, and a goniometer can be used thereof. In this case, measurement is performed by setting and scanning the X-ray incident angle θin, X-ray outgoing angle θout, and scattering angle 2θ=θin+θout. As in the case referred to as previously (see the steps s1 & s2 of the analyzing method), measuring the reflectance and measuring the scattering curve are respectively performed under θin=θout and under θin=θout±Δω with θout being scanned under θin being fixed or with θin being scanned under θ being fixed.

The density-nonuniform multilayer film analyzing apparatus (3) has critical angle getting means (31), function storage means (32), simulating means (33), and fitting means (34).

The critical angle getting means (31) derives the critical angle θc from the measured X-ray reflectance curve and actually measured X-ray scattering curve that have been measured by the X-ray measuring device (2), in the same way as previously referred to (see the step s3). Also, the apparatus (3) may be constructed so that δ can be calculated from that critical angle θc.

The function storage means (32) basically stores therein the above-described respective scattering functions. The above-described other expressions used in each of the respective scattering functions, of course, are also stored.

The simulating means (33), using the scattering functions (including the other necessary functions) supplied from the function storage means (32) and, further, θc (or δ) from the critical angle getting means (31), selects the values of various fitting parameters and calculates the simulated X-ray scattering curve in the same way (see the step s4) as that stated above.

The fitting means (34), in the same way (see the step s5) as stated above, performs fitting between the simulated X-ray scattering curve from the simulating means (33) and the actually measured X-ray scattering curve from the X-ray measuring device (2).

Data necessary for simulation and fitting such as the measured X-ray reflectance/scattering curves, θin/θout, and known quantities in the expressions 1 and 2, preferably, for example, is automatically sent out from the X-ray measuring device (2) to the density-nonuniform multilayer film analyzing apparatus (3), more concretely, to the critical angle getting means (31), simulating means (33), and fitting means (34) in corresponding relationship to each of those items of data. Of course, manual input is also possible.

As stated above, in the case where using the above-described respective expressions for calculating the simulated X-ray scattering curves, the simulating means (33) necessitates using various items of data including, other than θc (or δ), θin, θout, t, λ, μ, d, ρo, and, further, the known quantities in the expressions 1 and 2. For example, regarding θin and θout (or 2θ), each of them can be given by the X-ray measuring device (2) through automatic transmission while, on the other hand, regarding λ, μ, d, and ρo and the known quantities in the expressions 1 and 2, each of them can be given through manual inputting, previous storage, or calculation made separately. In the density-nonuniform multilayer film analyzing system (1) or density-nonuniform multilayer film analyzing apparatus (3), using input means, storage means, and calculating means for performing such operations is necessary. Needless to say, it is necessary that those kinds of means and the simulating means (33) be constructed in the way in which data transmission/reception can be made between them.

In the density-nonuniform multilayer film analyzing apparatus (3), in the same way (see the step s5 & s7) as stated before, until it is determined by the fitting means (34) that the simulated X-ray scattering curve and the actually X-ray scattering curve coincide with each other, calculating the simulated X-ray scattering curve while the above-described kinds of fitting parameters are being changed is performed by the simulating means (33). When the both curves coincide, the numerical values of the fitting parameters are analyzed as representing the actual state of distribution of the particulate matter.

In the example of FIG. 9, output means (35) is equipped to the density-nonuniform multilayer film analyzing apparatus (3) itself, or output means (36) is equipped to the density-nonuniform multilayer film analyzing system (1). And it is arranged that the analyzed results be output via those output means (35) and (36) such as a display, printer, built-in/separate storage means, etc. Also, in the case where causing the analyzed results, obtained by the density-nonuniform multilayer film analyzing system (1) or density-nonuniform multilayer film analyzing apparatus (3), to reflect in the production of a multilayer film or the like, it may be arranged that those analyzed results be able to be sent to a multilayer film production apparatus or a control device thereof.

The above-described density-nonuniform multilayer film analyzing apparatus (3) can be constructed into, for example, a software form that can be stored and started with a general-purpose computer or a computer for analysis only. In that case, each of the above-described means is realized as a program for executing a relevant one of them. Also, in the density-nonuniform multilayer film analyzing system (1), the density-nonuniform multilayer film analyzing apparatus (3) preferably is constructed in the way of the bi-directional or unidirectional signal transmission and reception's being able to be made between itself and the X-ray measuring device (2). Regarding selecting the optimum value of the fitting parameter by the simulating means (33), the apparatus (3) may have added thereto a function to automatically select by using the least square method, etc. so that the degree of coincidence between the simulated curve and the actually measured curve may become high (for example so that that may approach to a prescribed value). By doing so, analysis can be performed with full automation through the use of a computer, etc. In this case, of course, a form wherein arbitrary manual input can be performed may be adopted.

While the invention of the present application is the one that has the above-described features, Examples will hereafter be shown to thereby explain about the embodiment of the invention of the present application in further detail.

EXAMPLES

Example 1

As one example, analysis was performed of the pore (hole) state of distribution of a density-nonuniform multilayer film specimen wherein a porous film was laminated on a Si substrate. An explanation concerned therewith will be given below.

The film thickness of the multilayer film specimen was 600 nm and the pore density was 0.95 g/cm². For calculating the simulated X-ray scattering curve, there was used the transition probability-introduced scattering function prepared by the I(q)'s of the expression 12 being incorporated as the F(q) of the expression 4.

Figure 10:
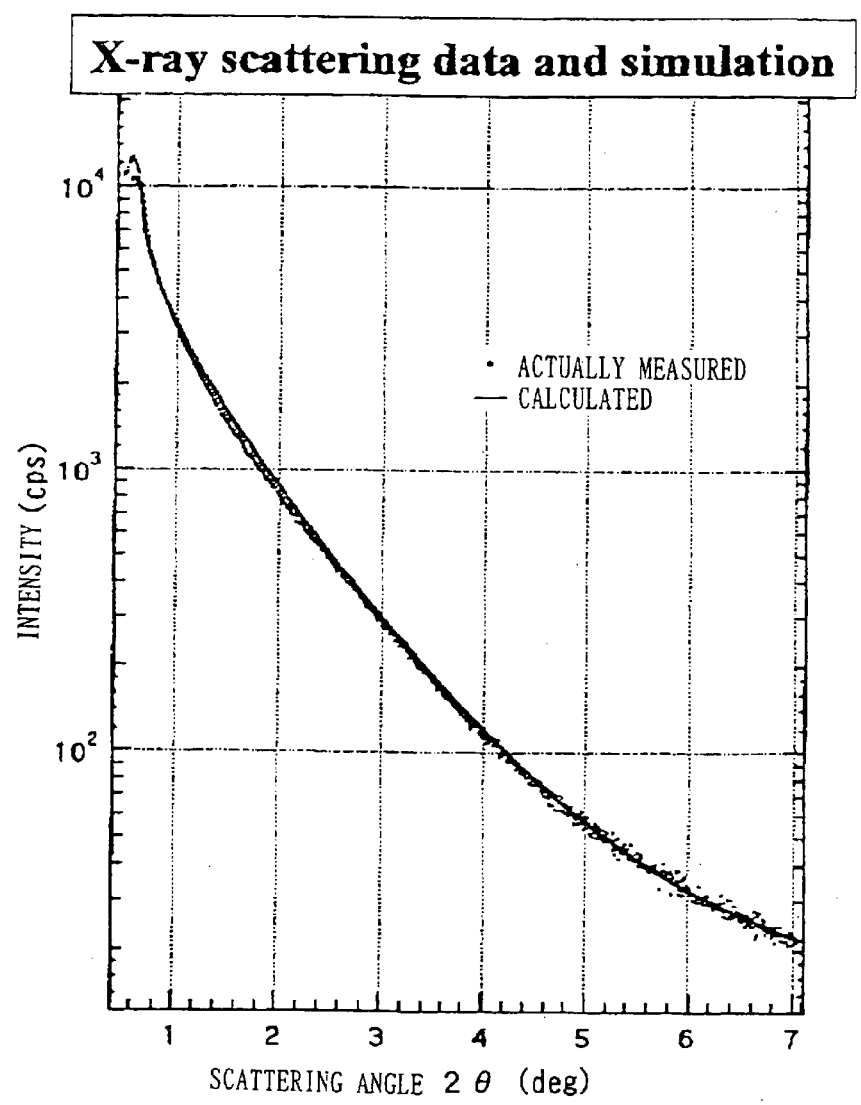
FIG. 10 is a graphic diagram illustrating the calculated/actually measured result of an X-ray scattering curve of a multilayer film specimen according to an embodiment of the invention of the present application.
Figure 11:
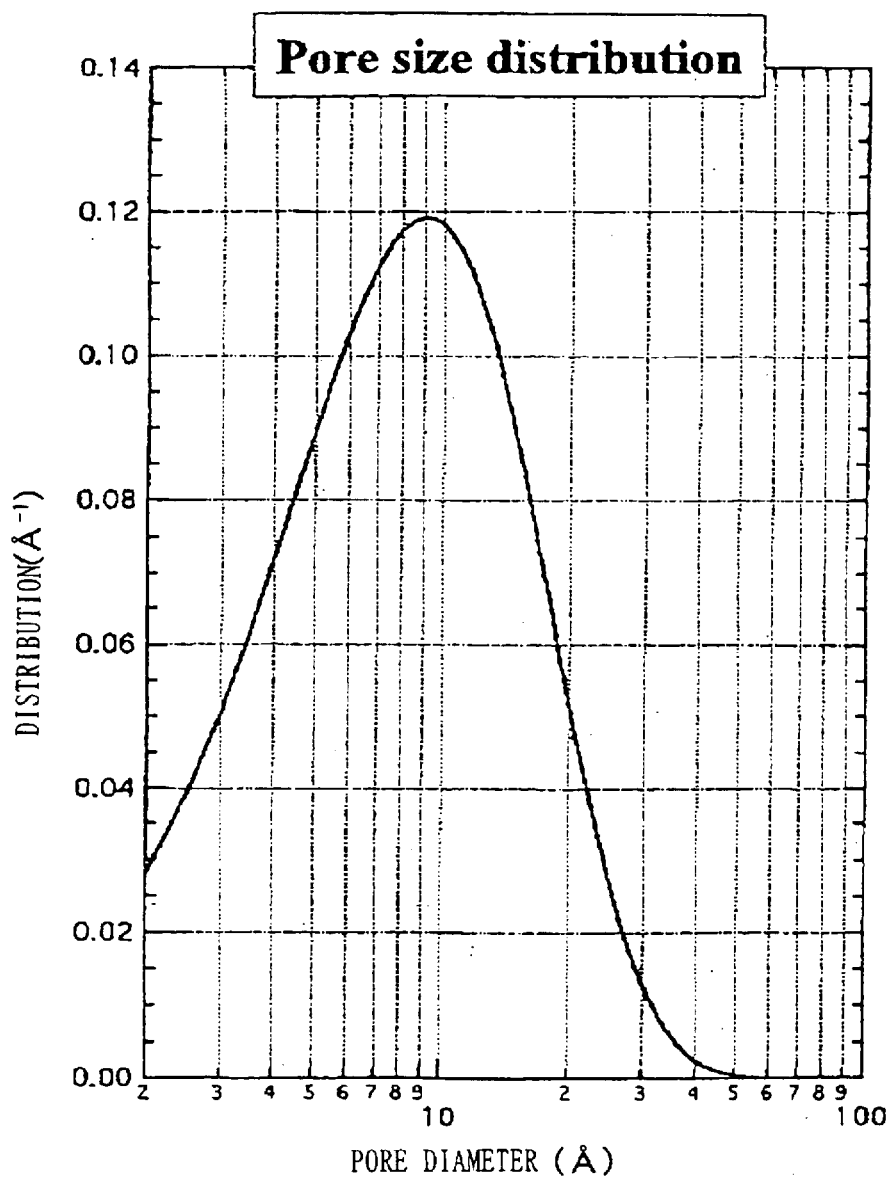
FIG. 11 is a view illustrating an analyzed result of the pore size distribution of a multilayer film specimen according to the embodiment of the invention of the present application.

FIG. 10 is a graphic diagram illustrating a simulated X-ray scattering curve obtained and an actually measured X-ray scattering curve in the way of the both being superposed one upon the other. As apparent from this FIG. 10, it exhibits a very high degree of coincidence between the both curves. The diameter parameter D and distribution spread parameter M at that time were D=1.4 nm and M=2.6 in terms of their optimum values, respectively. Accordingly, those respective values can be regarded as representing the average diameter value and distribution spread value of the pores in the multilayer film specimen that is the object to be analyzed of Example 1. FIG. 11 illustrates the distribution of the pore size (diameter) that has been obtained in that way.

Example 2

As another example, analysis was performed of a density-nonuniform multilayer film specimen wherein Low-k porous film was laminated on a Si substrate. The result will be explained below.

In this Example, measurement of an X-ray scattering curve was performed under $2\theta/(\theta+\Delta\theta)$ offset scan and under "0" rotation axis's-of-specimen scan with $2\theta$ being fixed (locking scan). Profile fitting was then performed using, with respect to the X-ray incident angle, outgoing angle, and strength data in each of those cases, the transition probability-introduced scattering function having the I(q) of the expression 11 incorporated as the F(q) of the expression 4 and the transition probability-introduced scattering function having introduced thereinto the fitting parameters representing the interfacial condition of the expression 30. By doing so, simultaneously with the analysis of the pore state of distribution in the multilayer film specimen, the analysis of the interfacial condition in each layer of the specimen is performed.

Figure 12:
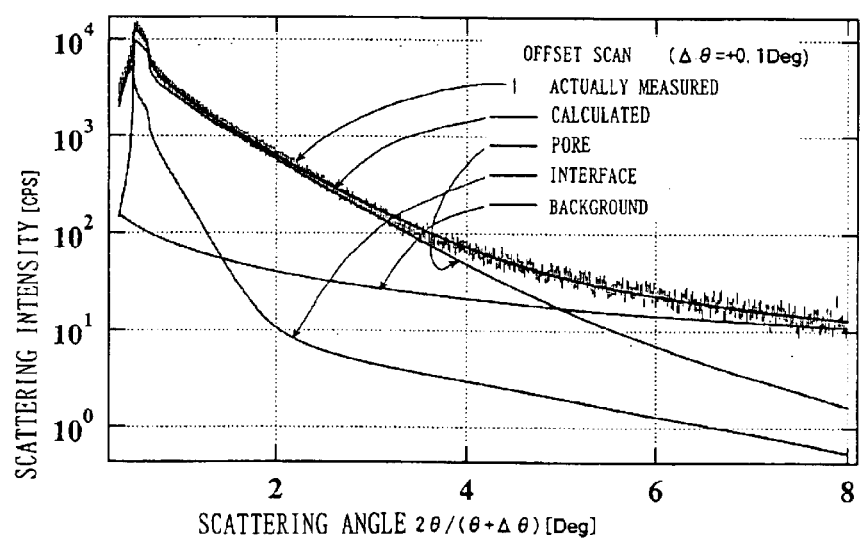
FIG. 12 is a view illustrating the calculated/actually measured result (offset scan) of a multilayer film specimen according to another embodiment of the invention of the present application.
Figure 13:
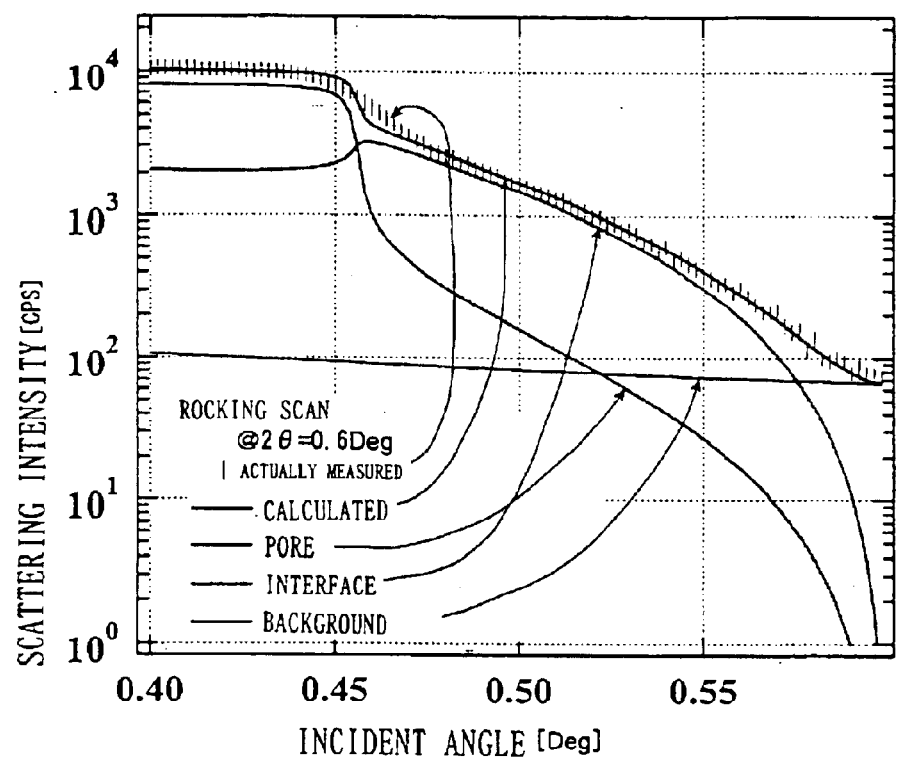
FIG. 13 is a view illustrating the calculated/actually measured result (rocking scan @ $2\theta=0.6°$) of an X-ray scattering curve of a multilayer film specimen according to another embodiment of the invention of the present application.
Figure 14:
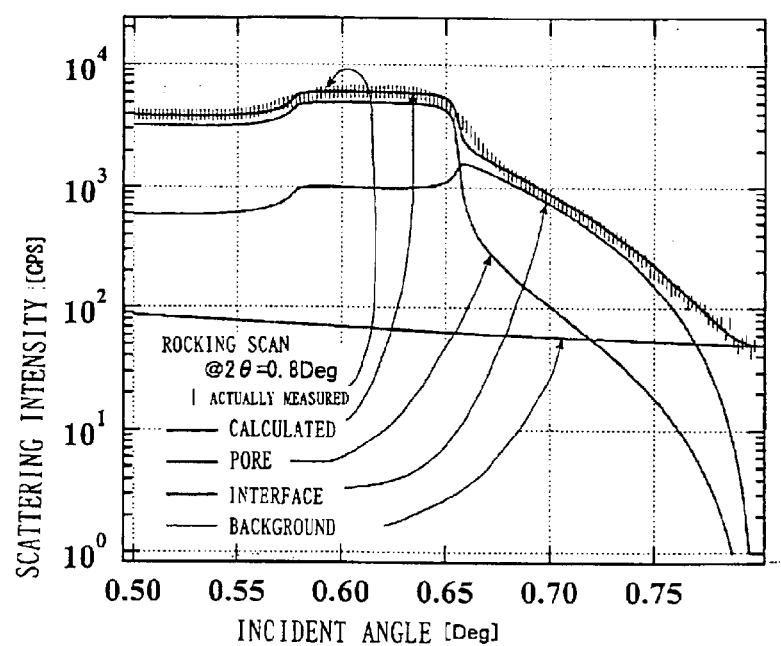
FIG. 14 is a view illustrating the calculated/actually measured result (rocking scan @ $2\theta=0.8°$) of an X-ray scattering curve of a multilayer film specimen according to still another embodiment of the invention of the present application.
Figure 15:
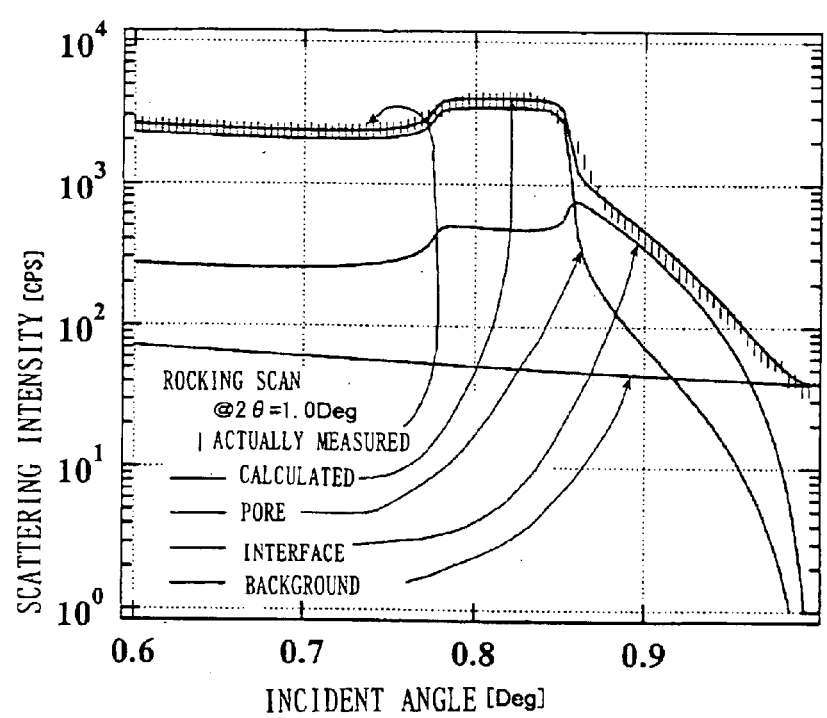
FIG. 15 is a view illustrating the calculated/actually measured result (rocking scan @ $2\theta=1.0°$) of an X-ray scattering curve of a multilayer film specimen according to still another embodiment of the invention of the present application.
Figure 16:
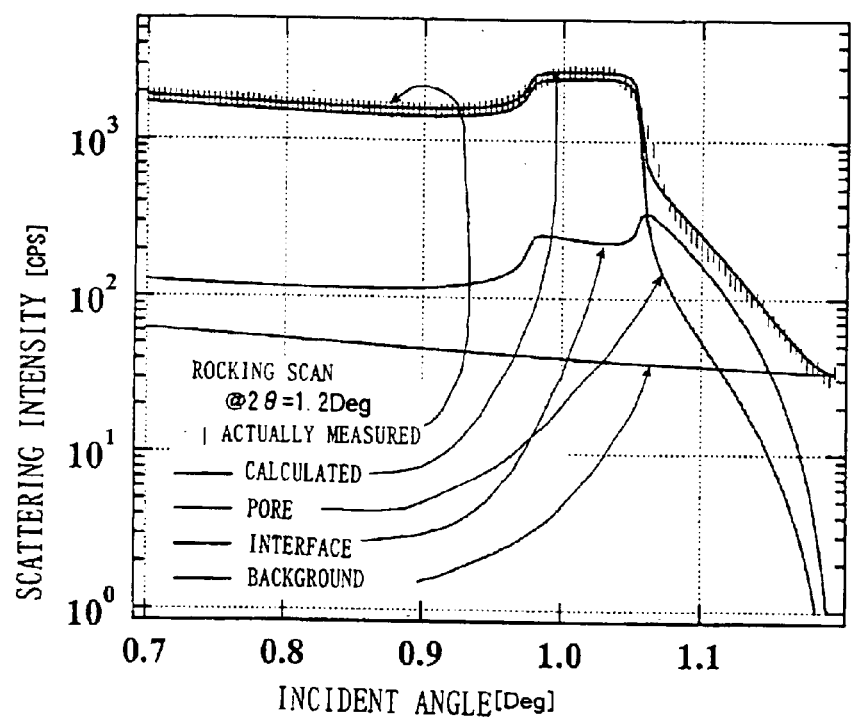
FIG. 16 is a view illustrating the calculated/actually measured result (rocking scan @ $2\theta=1.2°$) of an X-ray scattering curve of a multilayer film specimen according to still another embodiment of the invention of the present application.
Figure 17:
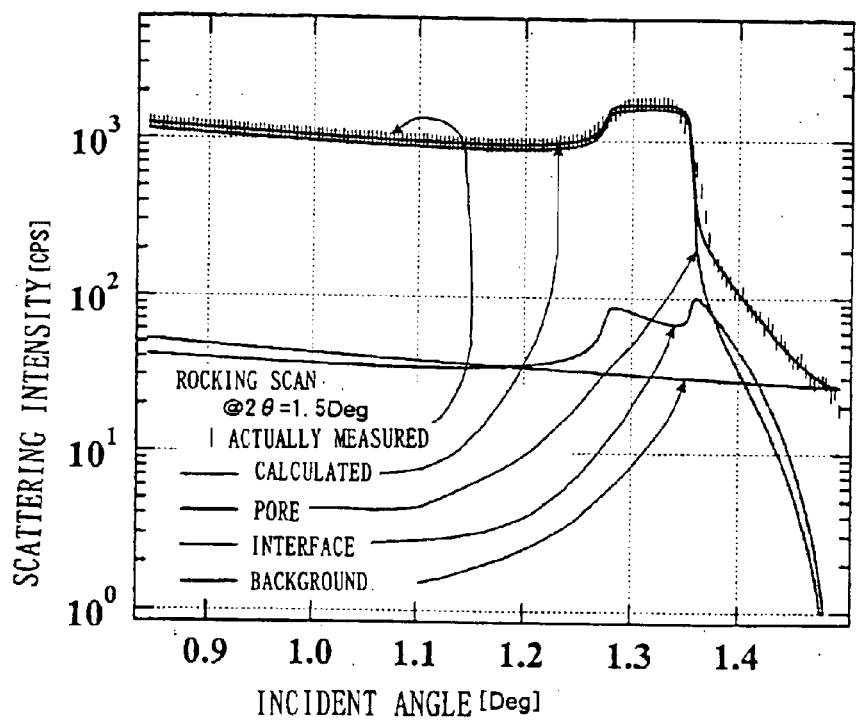
FIG. 17 is a view illustrating the calculated/actually measured result (rocking scan @ $2\theta=1.5°$) of an X-ray scattering curve of a multilayer film specimen according to still another embodiment of the invention of the present application.
Figure 18:
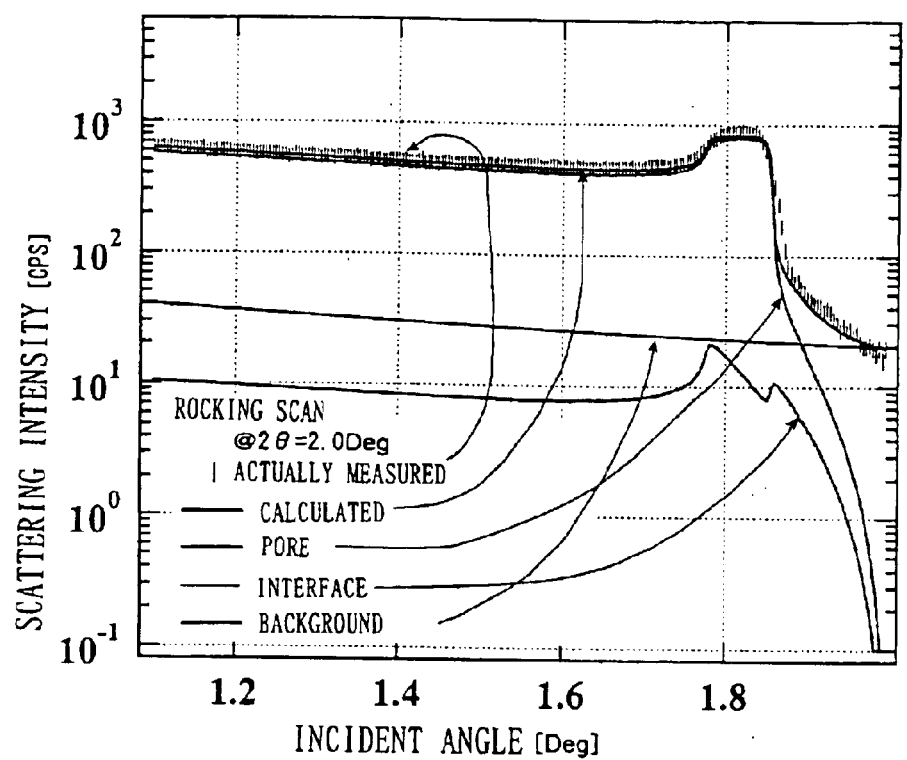
FIG. 18 is a view illustrating the calculated/actually measured result (rocking scan @ $2\theta=2.0°$) of an X-ray scattering curve of a multilayer film specimen according to still another embodiment of the invention of the present application.

FIG. 12 illustrates the data obtained when having performed offset scan under $2\theta/(\theta+\Delta\theta)$, which includes an actually measured X-ray scattering curve (the "actually measured" in the figure), simulated X-ray scattering curves (the "calculated" in the figure) obtained by adding together a simulated X-ray scattering curve according to the expressions 4 and 11 and a simulated X-ray scattering curve according to the expression 30, a simulated X-ray scattering curve (the "pore" in the figure) according to the expressions 4 and 11, a simulated X-ray scattering curve (the "interface" in the figure) according to the expression 30, and a background scattering curve (the "background" in the figure).

Each of FIGS. 13 to 18 illustrates the data obtained when having performed locking scan under $2\theta$ being fixed in the way of $2\theta=0.6°$, $0.8°$, $1.0°$, $1.2°$, $1.5°$, and $2.0°$, which includes an actually measured X-ray scattering curve (the "actually measured" in the figure), simulated X-ray scattering curves (the "calculated" in the figure) obtained by adding together a simulated X-ray scattering curve according to the expressions 4 and 11 and a simulated X-ray scattering curve according to the expression 30, a simulated X-ray scattering curve (the "pore" in the figure) according to the expressions 4 and 11, a simulated X-ray scattering curve (the "interface" in the figure) according to the expression 30, and a background scattering curve (the "background" in the figure).

In each of FIGS. 12 to 18, the simulated X-ray scattering curve added with "pore" in the figure is a scattering curve calculated using the expression 12 and is the one wherein the effect of the pore state of distribution is taken into consideration according to the fitting parameters [R, M] values. The simulated X-ray scattering curve added with "interface" in the figure is a scattering curve calculated using the expression 30 and is the one wherein the effect of the interfacial condition is taken into consideration according to the values of the fitting parameters [$\sigma$, $\xi$, h], and the simulated X-ray scattering curve added with "calculated" in the figure is a scattering curve obtained by adding together both of them and is the one to which both the pore state of distribution and the interfacial condition are given consideration simultaneously.

In any of the Figures referred to as above, it is seen that, by considering both of the pore state of distribution and the state of interface, a simulated X-ray scattering curve that has a very high degree of coincidence with respect to the actually measured X-ray scattering curve is obtained. The optimum values of the respective fitting parameters [R, M] and [$\sigma$, $\xi$, h] in the expressions 4, 11, and 30 at that time were as in Tables 1 and 2. Accordingly, these values can be regarded as being the average hole diameter, hole distribution spread, and the interfacial roughness, in-surface correlation length, and Hurst parameter of the multilayer film specimen that is the object to be analyzed in Example 2.

Table 1

| Average pore diameter R [nm] | 2.21 |
|---|---|
| Pore diameter at max probability [nm] | 1.8 |
| Shape parameter of size distribution M | 5.29 |

Table 2

| | | |
|---|---|---|
| Low-k porous film | Roughness $\sigma_0$ [nm] | 1.82484 |
| | lateral correlation length $\xi_0$ [nm] | 14.968 |
| | Hurst parameter $h_0$ | 0.5 |
| Si substrate | Roughness $\sigma_1$ [nm] | 0.221285 |
| | lateral correlation length $\xi_1$ [nm] | 11.611 |
| | Hurst parameter $h_1$ | 0.5 |

Figure 19:
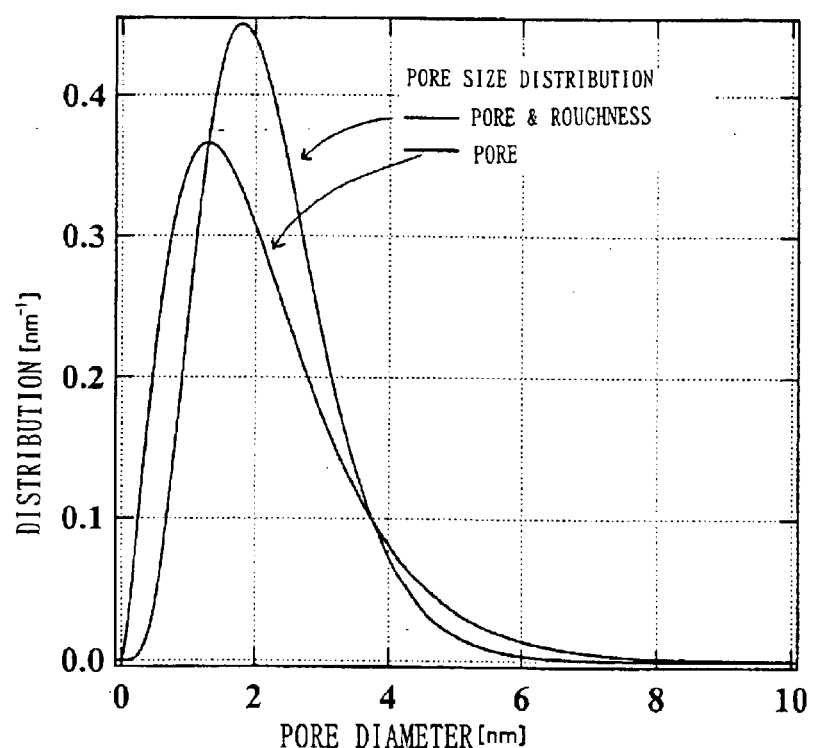
FIG. 19 is a view illustrating the analyzed result of the pore size distribution of a multilayer film specimen according to a yet further embodiment of the invention of the present application.

FIG. 19 illustrates the pore size distribution obtained using the above-described respective parameters. As seen in this FIG. 19, although there is the difference in terms of the pore size distribution between a case where both of the pore state of distribution and the state of interface are considered (the "pore & roughness" in the figure) and a case where only the pore state of distribution is considered (the "pore" in the figure), the former exhibits a more accurate level of pore size distribution. Pore diameter at max probability (pore diameter) in Table 1 above represents the peak value of the former graph.

Also, as apparent from Example 2 as well, according to the invention of the present application, it is possible to analyze only the scattering phenomena, alone, due to the interfacial condition, or it is also possible to compare and study the degree of the effect of the interfacial condition and pore state of distribution upon the X-ray scattering. Namely, the invention enables realizing the density-nonuniform multilayer film analysis with a high degree of accuracy and with a high degree of freedom.

Of course, the invention of the present application is not limited to the examples illustrated in the accompanying drawings but permits various types of modifications to be made in regard to the details.

As has been explained above in detail, the density-nonuniform multilayer film analyzing method, density-nonuniform multilayer film analyzing apparatus, and density-nonuniform multilayer film analyzing system according to the invention of the present application enables easily and highly accurately analyzing the state of distribution, and the interfacial condition, of the particulate matter within a density-nonuniform multilayer film where one or more layer of density-nonuniform film are laminated on a substrate, realizing a high degree of accuracy of evaluation with respect to the multilayer film specimen, and thereby can greatly contribute to the development of the multilayer film design/manufacture, etc.

What is claimed is:

1. A density-nonuniform multilayer analyzing method comprising the step of, by using a scattering function representing an X-ray scattering curve according to a fitting parameter indicating a state of distribution of particulate matter, calculating a simulated X-ray scattering curve under the same conditions as those under which an actually measured X-ray scattering curve is measured, and the step of performing fitting between the simulated X-ray scattering curve and the actually measured X-ray scattering curve while the fitting parameter is being changed, the values of the fitting parameters that have been used when the simulated X-ray scattering curve and the actually measured X-ray scattering curve have coincided with each other being regarded as representing the state of distribution of the particulate matter in the density-nonuniform multilayer film, to thereby analyze the state of distribution of the particulate matter within the density-nonuniform multilayer film, wherein as the scattering function, there is used a function into which there has been introduced the transition probability wherein the exact solutions of the multilayer film are set to be an initial state and a final state.

2. The density-nonuniform multilayer analyzing method according to claim 1, wherein, as the scattering function, there is used the transition-probability introduced function into which there has further been introduced a fitting parameter representing an interfacial condition.

3. The density-nonuniform multilayer analyzing method comprising the step of, by using a scattering function representing a corpuscular-ray scattering curve according to a fitting parameter indicating a state of distribution of particulate matter, calculating a simulated corpuscular-ray scattering curve under the same conditions as those under which an actually measured corpuscular-ray scattering curve is measured, and the step of performing fitting between the simulated corpuscular-ray scattering curve and the actually measured corpuscular-ray scattering curve while the fitting parameter is being changed, the values of the fitting parameters that have been used when the simulated corpuscular-ray scattering curve and the actually measured corpuscular-ray scattering curve have coincided with each other being regarded as representing the state of distribution of the particulate matter in the density-nonuniform multilayer film, to thereby analyze the state of distribution of the particulate matter within the density-nonuniform multilayer film, wherein as the scattering function, there is used a function into which there has been introduced the transition probability wherein the exact solutions of the multilayer film are set to be an initial state and a final state.

4. The density-nonuniform multilayer analyzing method according to claim 3, wherein, as the scattering function, there is used the transition-probability introduced function into which there has further been introduced a fitting parameter representing an interfacial condition.

5. A density-nonuniform multilayer analyzing apparatus comprising function storage means for storing therein a scattering function representing an X-ray scattering curve according to a fitting parameter indicating a state of distribution of particulate matter, simulating means for, by using a scattering function representing sent from the function storage means, calculating a simulated X-ray scattering curve under the same conditions as those under which an actually measured X-ray scattering curve is measured, and fitting means for performing fitting between the simulated X-ray scattering curve and the actually measured X-ray scattering curve while the fitting parameter is being changed, the values of the fitting parameters that have been used when the simulated X-ray scattering curve and the actually measured X-ray scattering curve have coincided with each other being regarded as representing the state of distribution of the particulate matter in the density-nonuniform multilayer film, to thereby analyze the state of distribution of the particulate matter within the density-nonuniform multilayer film, wherein the scattering function is a function into which there has been introduced the transition probability wherein the exact solutions of the multilayer film are set to be an initial state and a final state.

6. The density-nonuniform multilayer analyzing apparatus according to claim 5, wherein the scattering function is the transition-probability introduced function into which there has further been introduced a fitting parameter representing an interfacial condition.

7. A density-nonuniform multilayer analyzing system being adapted to analyze a state of distribution of particulate matter within a density-nonuniform multilayer film, comprising an X-ray measuring device for measuring an actually measured X-ray scattering curve of the density-nonuniform multilayer film and a density-nonuniform multilayer analyzing apparatus according to claim 6.

8. The density-nonuniform multilayer analyzing system being adapted to analyze a state of distribution of particulate matter within a density-nonuniform multilayer film, comprising a corpuscular-ray measuring device for measuring an actually measured corpuscular-ray scattering curve of the density-nonuniform multilayer film and the density-nonuniform multilayer analyzing apparatus according to claim 6.

9. A density-nonuniform multilayer analyzing system being adapted to analyze a state of distribution of particulate matter within a density-nonuniform multilayer film, comprising an X-ray measuring device for measuring an actually measured X-ray scattering curve of the density-nonuniform multilayer film and a density-nonuniform multilayer analyzing apparatus according to claim 5.

10. The density-nonuniform multilayer analyzing apparatus comprising function storage means for storing therein a scattering function representing a corpuscular-ray scattering curve according to a fitting parameter indicating a state of distribution of particulate matter, simulating means for, by using a scattering function representing sent from the function storage means, calculating a simulated corpuscular-ray scattering curve under the same conditions as those under which an actually measured corpuscular-ray scattering curve is measured, and fitting means for performing fitting between the simulated corpuscular-ray scattering curve and the actually measured corpuscular-ray scattering curve while the fitting parameter is being changed, the values of the fitting parameters that have been used when the simulated corpuscular-ray scattering curve and the actually measured corpuscular-ray scattering curve have coincided with each other being regarded as representing the state of distribution of the particulate matter in the density-nonuniform multilayer film, to thereby analyze the state of distribution of the particulate matter within the density-nonuniform multilayer film, wherein the scattering function is a function into which there has been introduced the transition probability wherein the exact solutions of the multilayer film are set to be an initial state and a final state.

11. The density-nonuniform multilayer analyzing system being adapted to analyze a state of distribution of particulate matter within a density-nonuniform multilayer film, comprising a corpuscular-ray measuring device for measuring an actually measured corpuscular-ray scattering curve of the density-nonuniform multilayer film and the density-nonuniform multilayer analyzing apparatus according to claim 10.

12. The density-nonuniform multilayer analyzing apparatus according to claim 10, wherein the scattering function is the transition-probability introduced function into which there has further been introduced a fitting parameter representing an interfacial condition.

* * * * *